(12) United States Patent
Drevik

(10) Patent No.: US 7,601,144 B2
(45) Date of Patent: *Oct. 13, 2009

(54) ABSORBENT ARTICLE WITH IMPROVED FIT

(75) Inventor: Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 393 days.

This patent is subject to a terminal disclaimer.

(21) Appl. No.: 10/310,907

(22) Filed: Dec. 6, 2002

(65) Prior Publication Data

US 2003/0125700 A1  Jul. 3, 2003

(51) Int. Cl.
 *A61F 13/15* (2006.01)
(52) U.S. Cl. .......................... 604/385.101; 604/385.17; 604/378; 604/380; 604/385.21; 604/379
(58) Field of Classification Search .......... 604/385.101, 604/385.01, 385.17, 378, 380, 379, 385.21, 604/371

See application file for complete search history.

(56) References Cited

U.S. PATENT DOCUMENTS

| | | |
|---|---|---|
| 3,294,091 A | 12/1966 | Morse |
| 4,285,343 A | 8/1981 | McNair |
| 4,608,047 A | 8/1986 | Mattingly |
| 4,655,759 A | 4/1987 | Romans-Hess et al. |
| 4,804,380 A | 2/1989 | Lassen et al. |
| 4,886,513 A | 12/1989 | Mason, Jr. et al. |
| 5,730,737 A | 3/1998 | Widlund et al. |
| 6,210,385 B1 | 4/2001 | Mizutani |
| 6,350,257 B1 | 2/2002 | Björklund et al. |
| 6,740,069 B2 * | 5/2004 | Drevik .................. 604/385.01 |

FOREIGN PATENT DOCUMENTS

| | | |
|---|---|---|
| EP | 0 067 465 | 12/1982 |
| EP | 0 130 848 | 1/1985 |
| EP | 0 134 086 | 3/1985 |
| EP | 0 155 515 | 9/1985 |
| EP | 0 298 348 | 1/1989 |
| EP | 0 335 252 | 10/1989 |
| EP | 0 335 253 | 10/1989 |
| EP | 0 336 578 | 10/1989 |
| EP | 0 852 938 | 7/1998 |
| EP | 0 956 844 | 11/1999 |
| EP | 9 965 318 | 12/1999 |
| FR | 2 653 328 | 4/1991 |
| SE | 455 668 | 8/1988 |
| SE | 507 798 | 7/1998 |
| WO | WO 97/09014 | 3/1997 |
| WO | WO 99/25282 | 5/1999 |

* cited by examiner

*Primary Examiner*—Jacqueline F. Stephens
(74) *Attorney, Agent, or Firm*—Buchanan Ingersoll & Rooney PC

(57) ABSTRACT

Absorbent article, such as a sanitary towel, with a stiffening area which is intended to contribute to the three-dimensional shape of the article during its use. The stiffening area is in a plane state before use of the article. The stiffening area comprises a first part area and a second part area which extends in the longitudinal direction of the article over the crotch portion and is separate from the first part area. The first stiffening part area has a width which exceeds the distance between the muscle tendons of the wearer on both sides of the crotch of the wearer in the groin of the latter.

38 Claims, 13 Drawing Sheets

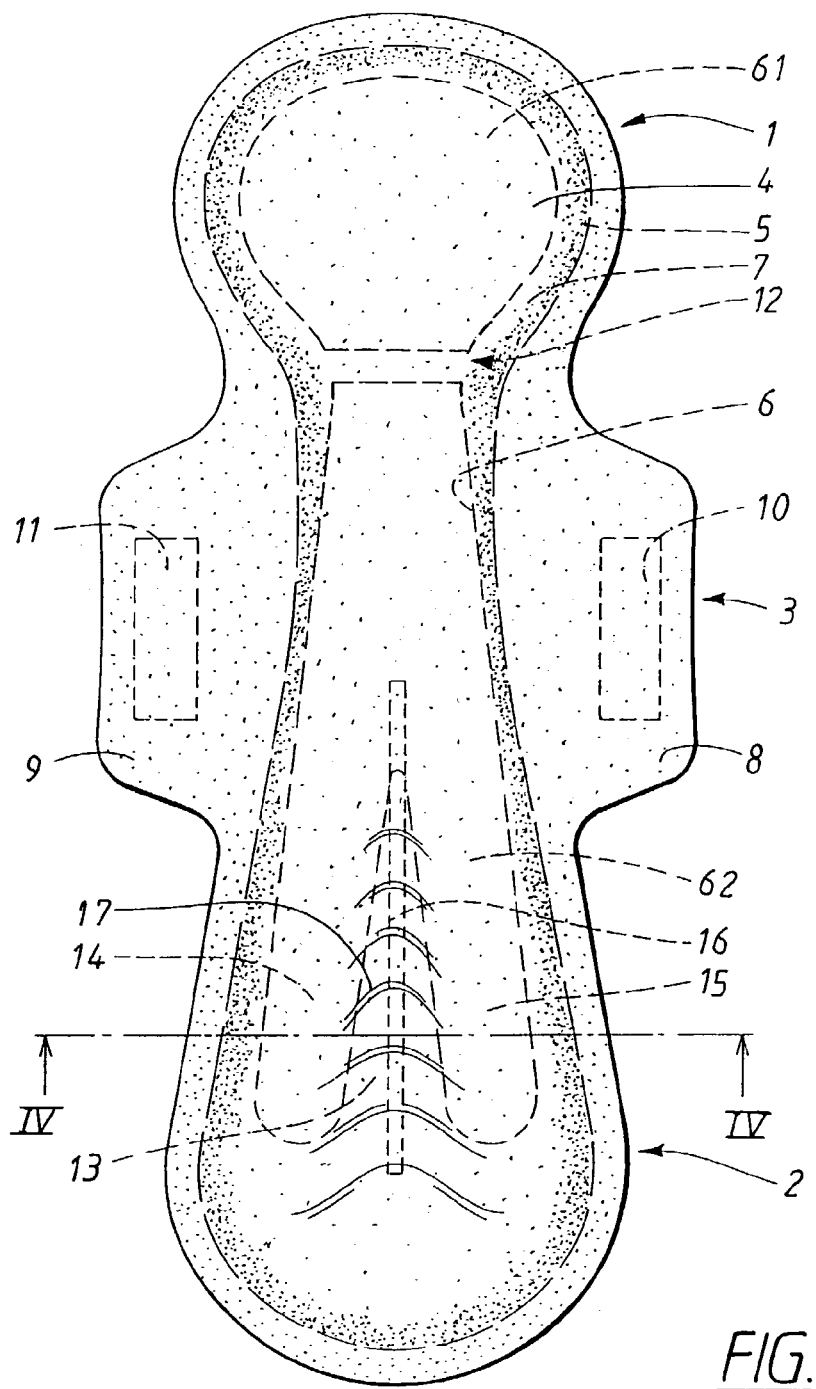
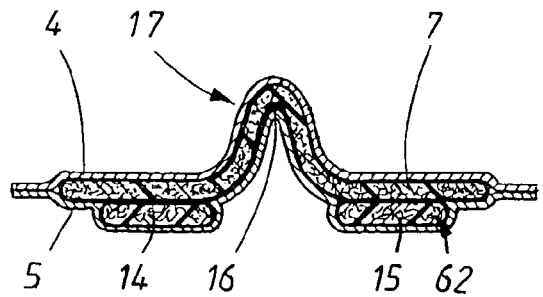

ABSORBENT ARTICLE WITH IMPROVED FIT

TECHNICAL FIELD

The present invention relates to an absorbent article, such as a sanitary towel, a panty liner, an incontinence pad, a nappy or the like, which article has a longitudinal direction and a transverse direction, a front portion, a rear portion, a crotch portion located between the rear portion and the front portion, an absorbent element and a liquid-tight layer, and also a stiffening element which is intended to contribute to the three-dimensional shape of the article during its use.

BACKGROUND OF THE INVENTION

A great many different demands are made of absorbent articles, such as a sanitary towel, an incontinence pad, a nappy or the like, which are not easy to satisfy simultaneously. A fundamental requirement is that the article, for example a sanitary towel, should be capable of catching and absorbing bodily fluid discharged from the wearer. Conventional sanitary towels in sizes intended for heavy flows of menstrual fluid have been of thick and relatively wide design. Sanitary towels of this type are described in, for example, U.S. Pat. No. 3,294,091. Thick and relatively wide sanitary towels of this type theoretically have great absorption capacity but in practice, when the sanitary towel is subjected to compression forces when squeezed together between the thighs of the wearer, much of the take-up capacity and absorption capacity is lost. The sanitary towel is squeezed together into an arbitrary rope-like shape which frequently does not offer a sufficiently large receiving surface for the menstrual fluid discharged, and leakage occurs in the case of heavy flows of menstrual fluid. The sanitary towel can also be pressed together between the thighs of the wearer in such a manner that the side edges of the sanitary towel and the liquid-tight layer are folded in over the liquid-permeable surface and in this way reduce the size of the liquid-receiving surface available.

Sanitary towels are intended to be positioned inside a pair of briefs, the design of which may vary. In this connection, sanitary towels can be positioned incorrectly inside the briefs. There is therefore a risk of the sanitary towel being, by mistake, positioned too far forward or too far back or displaced slightly in the lateral direction; and therefore, the absorption capacity and receiving surface of the entire sanitary towel may not be optimally utilized.

Conventional sanitary towels are generally retained in the briefs of the wearer by means of pressure-sensitive adhesive or friction coatings. The sanitary towel is fitted by the towel being put in place in the briefs, after which the latter are pulled up into position. When fitting the article inside the briefs, however, it is difficult to achieve a positioning which is optimum in relation to the body of the wearer. Use is usually made of the crotch portion of the briefs in order to determine where the sanitary towel should be positioned. As sanitary towels are manufactured in a great many sizes and models, the position and design of the crotch portion provide a particularly uncertain indication of where in the briefs a sanitary towel is to be positioned, and the functioning of the sanitary towel during use is consequently not always as desired.

Another cause of leakage occurring past sanitary towels attached inside the briefs of the wearer is that the sanitary towel moves together with the briefs instead of following the body movements of the wearer. This means that even a sanitary towel which was from the outset positioned correctly in the briefs in relation to the body can be pulled out of this position by the briefs.

In order to attempt to reduce leakage arising as a result of the sanitary towel being pressed together between the legs of the wearer, it has become usual to provide the sanitary towels with special attachment flaps. It is known from, for example, SE 455 668, U.S. Pat. No. 4,285,343, EP 0 130 848, EP 0 134 086 and U.S Pat. No. 4,608,047 to provide sanitary towels with flexible side flaps or wings projecting from the longitudinal side edges. These are intended to be folded around the edge portions of the briefs of the wearer when the sanitary towel is put on, and to be attached to the outside of the briefs. The side flaps themselves constitute protection against side edge leakage and soiling of the briefs. Moreover, deformation of the absorption body of the sanitary towel is counteracted by virtue of the fact that the sanitary towel is anchored at the leg edges of the briefs and is held extended between these during use.

However, a considerable disadvantage of providing absorbent articles with such attachment flaps is that many wearers find it embarrassing that the attachment flaps are visible on the outside of the briefs. This also means that absorbent articles with such attachment flaps cannot be used when, for example, the wearer is wearing a swimsuit.

Another disadvantage of the attachment flaps is that they are relatively difficult to handle and require many manual operations in order to be fitted correctly around the leg edges of the briefs. Furthermore, especially in the case of attachment flaps which extend quite a long way along the side edges of a sanitary towel, it can be virtually impossible to fold the attachment flaps around the curved leg edges of the briefs without chafing and unattractive creases in the attachment flaps occurring.

A further problem of sanitary towels with attachment flaps is that the functioning of the attachment flaps or wings depends on the design of the briefs. It goes without saying that a sanitary towel with attachment flaps interacts differently with briefs with a wide crotch compared with briefs with a very narrow crotch.

Attachment flaps or wings on sanitary towels protect the leg edges of the briefs from soiling but, for at least the reasons discussed above, are far from being an entirely satisfactory solution.

In order to improve leakproofness, EP 0 067 465 has proposed manufacturing a two-part sanitary towel in which the two parts are interconnected only at their end portions. The lower part is fastened in the briefs of the wearer, and the upper part makes contact with the body of the wearer. The idea is that the parts will be able to move slightly in relation to one another during use. The mobility between the parts is, however, very limited, and the known sanitary towel is still dependent on the movements of the briefs. Furthermore, there is no guarantee that the upper part will be held in contact with the body of the wearer during use.

PCT/SE96/01061 describes another two-part absorbent article in which the two parts are movable in relation to one another. This known article also has limited mobility between the parts and is to a certain extent dependent on the movements of the briefs.

One way of attempting to reduce the risk of edge leakage caused by deformation of the sanitary towel during use is to provide the sanitary towel with a preshaped raised portion, what is known as a hump, which is intended to make contact with the genitals of the wearer during use of the sanitary towel. Discharged bodily fluid can in this way be caught as soon as it leaves the body of the wearer and be absorbed immediately into the article instead of running out over the surface of the latter. A raised portion also makes it easier for the wearer to position the article correctly in relation to the body. French patent publication FR-A-2 653 328 describes a sanitary towel with a hump in the form of a central, longitudinal, cylindrical raised portion.

A common way of creating a raised portion has been quite simply to build it up by arranging a greater quantity of absorption material within the area of the raised portion. As the absorption material used is in most cases what is known as cellulose fluff pulp, however, such a raised portion collapses and loses its shape when it is wetted. In order to produce a raised portion which is sufficiently large in the wet state as well, a raised portion consisting of cellulose fluff pulp must comprise so much absorption material that it is altogether too high, hard and uncomfortable to wear in the dry state.

It is also known to produce an article with a raised portion facing the wearer by positioning a shaping element on top of the absorbent core. The disadvantage is that this interferes with the liquid transport down to the absorbent, liquid-retaining absorption core and that leakage can occur because the shaping element does not have sufficient admission capacity or temporary retention capacity. The use of, for example, a foamed material in the raised portion has been proposed. However, it has proved difficult to produce a foamed structure with sufficiently open pores for good liquid admission into the latter at the same time as the material is to have such great retention capacity that liquid is not pressed out in the event of loading originating from the wearer, for example when the wearer sits down.

Another example of a raised portion is described in Swedish patent 507 798. Such a raised portion has a predictable shape, both before and during use, and also keeps its shape irrespective of the movements of the wearer and of the wetting to which it is subjected. The raised portion is anatomically designed, which means that it is relatively narrow in order to project in slightly between the labia of the wearer during use without causing discomfort for the wearer.

Although such a raised portion functions well for its purpose, it has been found that when the raised portion is exposed to large quantities of bodily fluid over a relatively short period of time, there is a risk that some of the liquid will run on the outside of the raised portion and flow out past the side edges of the absorbent article. Such leakage can occur, for example, when the wearer of a sanitary towel has been sitting or lying down for a relatively long period of time and then suddenly rises. This is because, when the wearer is sitting or lying down, a relatively large quantity of menstrual fluid accumulates in the vagina of the wearer. In the event of a sudden change in body position, the entire quantity of accumulated liquid may be discharged at once. A narrow raised portion of the type described in SE 507 798 does not then have a sufficiently large surface to be capable of receiving and absorbing the entire quantity of liquid at one time, for which reason such sudden liquid flows often result in leakage.

EP 0 335 252 and EP 0 335 253 have proposed providing an absorbent article with a deformation element. The deformation element is acted on by the transverse compressive forces between the thighs of a wearer. The purpose of the deformation element is to cause a portion of the article to bulge in the direction of the body of the wearer during use. It is impossible, however, to control or predict entirely the shape the article will adopt for each individual wearer. Moreover, it is not possible to ensure contact between the body of the wearer and the surface of the article, because the degree of bulging is determined entirely by how much the article is compressed in the transverse direction.

U.S. Pat. No. 4,804,380 describes an absorbent article which has a permanent three-dimensional shape. The article has one end portion of flat or concave shape and one end portion provided with a raised portion. The flat or concave end portion is intended to be positioned in front of the mons Veneris of the wearer, and the end portion comprising the raised portion is intended to fit in against the buttocks of the wearer. The three-dimensional design of the article is brought about by folding a fairly stiff absorption body. In order to make the raised portion permanent, the rear side of the article is provided with a glued surface in the end portion which is to have the raised portion. When the raised portion has been formed, it is maintained by means of the glue.

There are absorbent articles on the market which have a permanent, three-dimensional, boat-like shape and in which the outer shell consists of a moulded polymer foam.

A considerable disadvantage of permanent three-dimensional products is that it is difficult to pack a stiff three-dimensional product. Such products require a great deal of space for transport and sale, and it can be embarrassing for a wearer to carry around a sanitary towel or an incontinence pad when it is impossible to fold and therefore cannot be concealed in the hand or in the worst case will not even fit in a handbag.

EP 155 515 describes how an absorbent article, such as a sanitary towel, is provided with a bowl-shaped appearance by virtue of elastic being applied in a pretensioned state at the longitudinal side edges of the article. However, the use of such elastic complicates manufacture.

It is previously known to design plane absorbent articles which adopt a three-dimensional, essentially bowl-like shape when applied. An example of this is described in U.S. Pat. No. 4,655,759, which discloses an elongate sanitary towel consisting of a layer of absorbent material, a flexible liquid-tight outer layer and a liquid-permeable inner layer. The sanitary towel is provided with a pair of channels formed by stamping, the channels being located on both sides of a longitudinal centre axis and extending along a curved path over the absorption material layer. The two paths together form an hourglass-like shape positioned centrally over the towel. Before use, the sanitary towels are essentially plane but, when they are applied to the wearer, they are folded into a bowl-like shape, that is to say with liquid-stopping upright borders outside the channels. One disadvantage of this bowl-like construction is that the borders hold the central portion of the sanitary towel at a distance from the genitals of the wearer, and liquid discharged from the wearer does not flow directly into the absorbent article but can run on the surface, the risk then being obvious that liquid may find an undesirable transport path in the form of a small crease or the like and run straight out of the product in the lateral or longitudinal direction. Stamped channels in an absorption body also have the disadvantage that the liquid spread in the absorption layer is disrupted and that absorption material outside the channels is not utilized, which increases the risk of local oversaturation and attendant leakage from those parts of the absorption layer which are used.

Previously known sanitary towels and the various problems associated with them have in the main been discussed above. However, what has been said above also applies to incontinence pads. Nappies for children and adults also belong to the same problem area as far as fit in the crotch and take-up of liquid in an absorption body are concerned.

As emerged above, great efforts have been made over many years in order to attempt to solve all the problems associated with absorbent articles, such as sanitary towels. Although great improvements have been made, all the previously known solutions are associated with some disadvantages.

SUMMARY OF THE INVENTION

By means of the present invention, an improved absorbent article of the type mentioned in the introduction has been produced. The article according to the invention is characterized mainly in that a stiffening area is in a plane state before use of the article, in that the stiffening area, seen in the longitudinal direction of the article, includes a first, front stiffening part area in the front portion of the article and at least one further, second stiffening part area which is separate from the first part area, in that, at least at the transition between the crotch portion and the front portion, a soft transition space is arranged between said stiffening part areas, and in that said separate first and second stiffening part areas and intermediate soft transition space are arranged so as to control the positioning of the article on the wearer, the width of the first part area exceeding the distance between the muscle tendons of the wearer on both sides of the crotch of the wearer in the groin of the latter, and the soft transition space being arranged to as to come to lie directly in front of said muscle tendons of the wearer.

An absorbent article according to the invention has a number of advantages. It is generally planar before use, and there are therefore no problems associated with packing, storing and transporting said article. An absorbent article according to the invention automatically adopts a three-dimensional bowl-like shape in an area in the front portion when the wearer puts the article on and fits it with said soft transition space between said muscle tendons where the available width space is narrowest. It is known that the distance between said muscle tendons is very similar for all people. Fatness of course has an effect on the width between the thighs, but the width between the muscle groups is the same, and it is these which may cause an article to feel as if it chafes. The fat tissue lies on the outside of the muscles but does not contribute to any sensation of discomfort. The distance between said muscle tendons is relatively the same irrespective of whether the wearer is slim, of normal weight or overweight. It has been found that what determines whether a wearer experiences discomfort in the form of pressure or chafing against the insides of the thighs is whether the absorbent article has a width during use which in this subject area considerably exceeds the distance between the muscle tendons in the groin portion. This distance between the muscle tendons has been found to be roughly 25-45 mm. It has been found that an article with a width which exceeds about 40 mm in the subject area during use feels uncomfortable to wear to the majority of wearers if the article is stiff in this area. On the other hand, it is rarely experienced as being unpleasant if an absorbent article pushes down or aside fat tissue which may be present in the crotch area of the wearer.

Surprisingly, it has been found that this distance between said muscle tendons does not change throughout the lifetime of a person. Small infants therefore have a corresponding subject distance, which, according to the present invention, can be utilized for producing nappies for infants with an improved fit. The same of course applies for nappies for adults. It should be pointed out that said subject distance between the muscle tendons applies for men also, who have the same distance between said muscle tendons.

An article designed according to the invention is adapted to the anatomy of the wearer. The soft transition space can be fitted between said muscle tendons without any risk at all of chafing in this area. The arrangement of the first, front stiffening part area in front of said muscle tendons results in an article being anchored firmly in the groins of the wearer during use, and in this way the article is prevented from moving backwards between the legs of the wearer. This is otherwise a common problem in conventional articles because the leg movements of the wearer often shift the article backwards.

The first and second stiffening part areas are separate from one another at the transition between the front portion and the crotch portion of the article, which gives rise to a bending indication in the area between the stiffening part areas. Along the crotch, the body shape of the wearer is essentially plane, and the second stiffening part area can therefore be essentially plane and stiff in the crotch area. In the area directly in front of the groins, the body curves abruptly in relation to the crotch in prolongation thereof, and the bending indication in the form of the absence of stiffening material in the gap between the first and second stiffening elements means that the article curves adjacently to the body of the wearer. As mentioned above, the geometry around the transition between the crotch portion and the front portion means that an article is anchored firmly with the relatively wide first part area in front of the muscle tendons in the groins of the wearer. This geometry results in the article virtually of necessity coming to lie in the correct place on the wearer. The folding indication which is created in the gap between the first and the second stiffening part areas also makes a considerable contribution to the article coming to lie in the correct place on the wearer. By virtue of the fact that the first part area is separate from the second stiffening part area, a certain turning of one part area in relation to the other is permitted, which makes increased mobility possible for the wearer without annoying chafing caused by the stiffening part areas.

According to one embodiment, the article according to the invention is characterized in that the distance between the first stiffening area and the second stiffening area is preferably at least 10 mm. According to another embodiment, the first and the second part area are separated from one another at said transition by a distance on the order of 15-45 mm.

According to one embodiment, the invention is characterized in that the width of the second part area close to said space or at least at some point along the crotch portion of the article exceeds the distance between the muscle tendons of a wearer on both sides of the crotch of the wearer in the groin of the latter. According to another embodiment, the invention is characterized in that the necessary distance between the stiffening part areas is controlled by the width of the front part area and by its contour.

By virtue of the first and the second part area being separated from one another by a distance, space is provided for the first and the second part element to expand in the longitudinal direction in said space when liquid is absorbed.

According to another embodiment, the invention is characterized in that the side edges of the first stiffening part area diverge in the direction from said transition, and in that the side edges of the first stiffening part area form, in the direction from the crotch portion, an acute angle with a line in the longitudinal direction of the article.

According to one embodiment, the invention is characterized in that said stiffening part areas consist of compressed part areas of a continuous material body made in one piece, which forms said soft space between said part areas.

According to one embodiment, the first and the second part areas are made from different materials. This increases the freedom to customize the article for different application requirements.

According to one embodiment, the first and the second part areas have different stiffnesses.

According to a further embodiment, the first and the second part areas have different absorption and swelling capacity.

According to one embodiment, the first part area is non-absorbent so as to maintain its three-dimensional shape during use.

According to another embodiment, the first part area is absorbent and the second part area is non-absorbent.

According to one embodiment, the first and the second part areas are connected by an elastic element. This means that the first and the second part areas can return to their intended relative position after turning or pulling-apart of the two parts area during use of the article.

According to one embodiment, the invention is characterized in that at least the second of said stiffening part areas is absorbent and at the same time constitutes the absorbent element, and in that it swells during absorption while on the whole retaining its geometry in the transverse direction of the article.

According to an especially preferred embodiment, the invention is characterized in that at least the second of said stiffening part areas is absorbent and at the same time constitutes the absorbent element, and in that it swells during absorption while retaining its geometry in the transverse direction of the article.

To form a stiffening area, it is of course possible to have one or more separate stiffening elements behind the absorption element, seen from the side facing the wearer. However, in terms of production, it is simpler if separate stiffening elements can be eliminated. It is of course also preferable from an environmental point of view.

According to one embodiment, at least one of the stiffening part areas has a stiffness on the order of 1-15 N measured according to ASTM D 4032-82. This "Circular Bend Procedure" is described in detail in EP 336 578, which corresponds to U.S. Pat. No. 4,950,264, the entire contents of which are hereby incorporated by reference.

According to one embodiment, the invention is characterized in that at least one of the stiffening part elements consists of a dry-formed fibre mat with a density between 0.15 and 0.75 g/cm$^3$ and a weight per unit area on the order of 100-400 g/m$^2$.

A dry-formed fibre mat of this kind is described in U.S. Pat. No. 5,730,737. The fibre mat produced is very stiff after forming and compression. The fibre mat can be used as it is or be mechanically softened to the desired stiffness.

A way of very accurately forming fibrous webs for use as absorption elements in absorbent articles is described in Swedish patent application 0101393-7. The fibrous webs are formed by air-laying fibres, separate air flows containing fibres being fed to a number "n" of different mat-forming wheels, where "n" is a whole number which is at least 2. Separate web layers are formed on the individual web-forming wheels. The fibrous web is formed by said web layers being combined to form a common fibrous web downstream of the mat-forming wheels, which web has very great manufacturing accuracy by virtue of the manufacturing method. The manufacturing speed and thus the web speed can be very high, and the desired manufacturing accuracy at the web speed concerned is achieved by selecting a sufficiently high number "n" of mat-forming wheels. By virtue of this manufacturing method, very thin fibrous webs can be manufactured with very great accuracy.

According to one embodiment, the article according to the invention is characterized in that the side edges of the first stiffening part area diverge at least part of the way from the crotch portion in over the front portion of the article and are arranged so as to form an angle between a line in the longitudinal direction of the article and each of said side edges on the order of about 35-55°, preferably on the order of about 45°. With this geometry in and around the transition between the crotch portion and the front portion, effective anchoring is obtained without the wearer experiencing any discomfort in the form of chafing or the like.

According to one embodiment, the article according to the invention is characterized in that the second stiffening part area also extends part of the way in over the rear portion of the article, and in that the side edges of the second stiffening part area diverge in the direction from the crotch portion at least part of the way from the crotch portion in over the rear portion of the article. The crotch portion suitably has a length of preferably about 70-120 mm. This length corresponds to the length of a plane portion in the crotch portion of a woman. The stiffening area according to the last embodiment is therefore anchored both at the front and at the rear at the transition between the crotch portion and the front portion and, respectively, at the transition between the crotch portion and the rear portion, as a result of which an article which is very stable, well fixed and at the same time comfortable during use is obtained.

According to one embodiment, the invention is characterized in that the second stiffening part area also extends part of the way in over the rear portion of the article, and in that the side edges of the second stiffening part area diverge in the direction from the crotch portion at least part of the way from the crotch portion in over the rear portion of the article.

According to one embodiment, the invention is characterized in that the second stiffening part area has in the rear portion a cutout extending from its end edge in the direction towards the crotch portion, as a result of which the article is during use provided with a fold along the longitudinal direction of the article in said cutout, which fold extends into the cleft between the buttocks of the wearer during use of the article.

According to a further embodiment, the invention is characterized in that the article is arranged so as, by virtue of the stiffness selected for said stiffening part area and by virtue of said geometry selected around the transition between the crotch portion and the front portion, when the article is positioned in connection with it being put on with the transition between the front portion and the crotch portion between said muscle tendons, to be fixed in between these and in this way be transformed from plane form to three-dimensional form with the front portion curved upwards in relation to the crotch portion and forming a bowl-like shape at least in an area next to the crotch portion.

Further advantageous embodiments of the article according to the invention emerge from the subsequent patent claims.

BRIEF DESCRIPTION OF THE FIGURES

The invention will be described in greater detail below with reference to illustrative embodiments shown in the accompanying drawings, in which:

FIG. 3 shows an embodiment, slightly modified in relation to the embodiment according to FIG. 1, of an article according to the invention in a plan view;

FIG. 4 shows a section along the line IV-IV in FIG. 3;

DETAILED DESCRIPTION OF THE INVENTION

Figure 1:
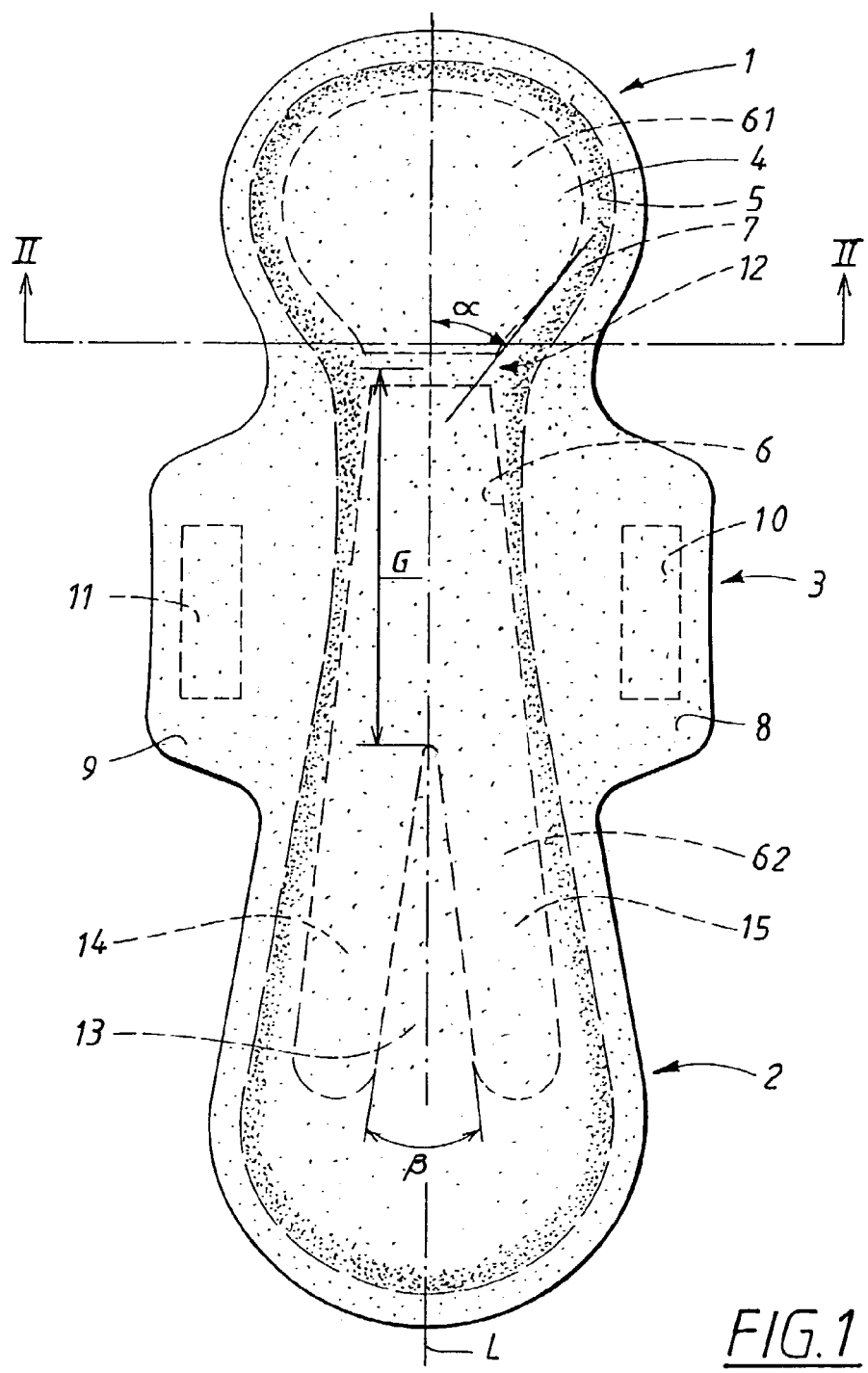
FIG. 1 shows a plan view of an absorbent article according to a first embodiment.
Figure 2:
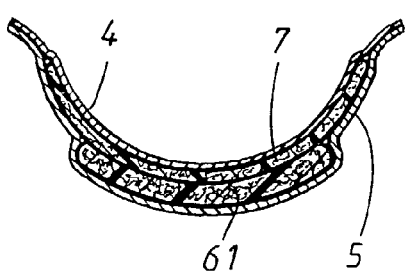
FIG. 2 shows a section along the line 11-11 in FIG. 1 but in a curved utilization state.

FIGS. 1 and 2 show an article according to the invention in the form of a sanitary towel or incontinence pad. The article is elongate with a longitudinal direction and a transverse direction. The article has a front portion 1, a rear portion 2 and a crotch portion 3 located between said portions. The article shown in FIGS. 1 and 2 comprises an inner layer 4, preferably liquid permeable, which is intended to face the wearer during use of the article. The inner layer, which makes contact directly with the skin of the wearer, is suitably made from a soft, textile-like material. Examples of suitable liquid-permeable materials are various types of what are known as non-woven fabrics. Other examples of suitable materials are perforated plastic films. Net and knitted or woven textiles as well as combinations and laminates of said materials can also be used as the inner layer. Examples of inner layers for sanitary towels are laminates of various non-wovens and laminates of non-wovens and perforated plastic films. The liquid-permeable layer can also be integrated with underlying drainage or absorption layers; for example a foam plastic with open pores and with a density gradient in the depth direction can serve as a surface layer and as a drainage layer and/or absorption layer.

The absorbent article also has a liquid-tight outer layer 5. This usually includes of a thin plastic layer, made of polyethylene for example. It is also possible to use a liquid-permeable material which has been treated with a hydrophobing agent in order to make it liquid-tight. In particular if the absorbent article is relatively large, it may be suitable for the outer layer to be vapour-permeable in addition to being liquid-tight. Such layers can consist of hydrophobed non-woven fabric or of porous plastic films.

The absorbent article includes an absorbent element 6 of on the whole keyhole-like shape, and a liquid-permeable insulating layer 7 which likewise has a keyhole-like shape but with a greater extent in both the longitudinal direction and the transverse direction than the absorbent element 6. The outer layer 5 and the inner layer 4 extend with edge portions outside the insulating layer around the latter and are interconnected along these edge portions to form a cover around the absorbent element 6 and the insulating layer 7. In the region of the crotch portion 3, the cover formed by the inner and outer layers extends outwards in the lateral direction to form flexible side flaps 8, 9, what are known as wings, which are intended to be arranged around the crotch portion on the briefs of the wearer in order to protect the edge portions of the briefs from soiling. The wings 8, 9 are suitably provided with adhesive coating, which has been indicated in FIG. 1 by reference numbers 10, 11, on the outer layer 5, by means of which the wings can be attached around the legs of the briefs. As can be seen from FIG. 2, the insulating layer 7 is located directly inside the inner layer 4 and is principally intended for rapidly admitting discharged bodily fluid into the underlying absorbent element 6 and forming a liquid-insulating layer so as to reduce what is known as back-wetting from the absorbent element 6 to the inner layer 4 making contact directly with the wearer.

The insulating layer can be made of, for example, an airlaid fibrous material of low density bonded together with bonding agent or thermofibre, which is marketed under the designation LDA (low density airlaid). The absorbent element 6 is, seen from the liquid-permeable inner layer 4, arranged under the insulating layer 7. In the illustrative embodiment shown here of the article according to the invention, this element is designed to take up and retain essentially all the bodily fluid discharged. The absorbent element 6 can be made from a material which has smaller capillaries than the insulating layer 7 located above and therefore draws liquid from the insulating layer and prevents back-wetting by liquid from the absorbent element to the insulating element and to the inner layer 4 which remains essentially dry during use of the article. Only when the absorbent element is saturated with liquid can transport take place from the absorbent element to the insulating layer.

The liquid-insulating layer 7 and the absorbent element 6 can of course be made from materials other than those indicated above. The important aspect is that the absorbent element 6 has greater liquid-affinity than the liquid-insulating layer 7 so that liquid is transported from the insulating layer to the absorbent element but not vice versa.

The liquid-insulating layer can be made of, for example, what is known as a multibond non-woven, that is to say a non-woven fabric in which fibres are bonded by both bonding agent and melt bonds. This can also contain fibres or particles made of a slow-acting superabsorbent material and/or an odour-inhibiting superabsorbent material.

In the illustrative embodiment shown, the absorbent element 6 is also intended to serve as a stiffening element and is to this end designed so as to be very stiff in order as far as possible to avoid the absorbent article being compressed in an uncontrolled manner when squeezing forces in the lateral direction occur, generated by the thighs of the wearer in the crotch area. The absorbent stiffening element has a size, shape and stiffness which result in the article, throughout its time of use, retaining a predetermined shape and moreover being retained in the intended position on the wearer.

The expression stiffening area means that an area has been reinforced in some way in order that this area is stiffer than the rest of the article. This reinforcement can include a separate reinforcing element which, as in the embodiment according to FIGS. 1 and 2, also serves as an absorbent element, or a completely separate stiffening element which has only a stiffening function and can include an element, made of paper or plastic for example, which is stiff in relation to the rest of the article and can be constructed from one or more material layers made of the same material or different materials. Alternatively, the stiffening area can be brought about by virtue of the article having been stiffened in this area by extra bonding agent between individual material plies. Alternatively, the article can be made of material which is permanently compressible at least in the area which is to be stiffened, suitable compression taking place during manufacture of the article to bring about the desired stiffness in the area concerned. The latter illustrative embodiment is described in greater detail below.

In the description below, the expressions stiffening area and stiffening element will be used interchangeably, the most suitable expression being selected in order to clarify what is meant at the point concerned in the text.

As can be seen from FIG. 1, the absorbent stiffening element 6 extends over the front portion, the entire crotch portion 3 and a considerable part of the rear portion 2.

The absorbent stiffening element 6 has a first, front part element 61, which has a width adapted to the crotch of the wearer, and a second part element 62, which is separate from the first part element 61, as a result of which the first and the second part element are movable in relation to one another. A soft transition space 120 between said stiffening part elements is arranged at the transition 12 between the crotch portion and the front portion.

Said first and second stiffening part elements 61, 62 and intermediate soft transition space are arranged so as to control the positioning of the article. At least at some point along the longitudinal direction of the article, the width of the first part area exceeds the distance between the muscle tendons of the wearer on both sides of the crotch of the wearer in the groin of the latter. The soft transition space 120 is arranged so as to come to lie directly in front of said muscle tendons of the wearer during use.

These muscle tendons form part of the muscle group which originates on the inside of the pelvic diaphragm and has its attachment along the thigh. This muscle group includes of the adductor brevis, adductor longus, gracilis and adductor magnus muscles. As mentioned above, it is known that the distance between said muscle tendons is very similar for all people. This dimension is on the order of 25-45 mm. Research has shown that 80% of all women have a dimension of 30-32 mm between said muscle tendons. When said width of the first part element exceeds the distance between said muscle tendons of the wearer, the article will, during its use and any attendant sliding backwards of the article when the wearer moves, be stopped in its backward sliding at that portion of the first part element of which the width exceeds the distance between the muscle tendons, and be anchored firmly between the muscle tendons and retained in this position. In the illustrative embodiment shown in FIG. 1, the two side edges of the first stiffening part element 61 diverge in the forward direction on the article from said transition area 12. The article is therefore prevented from moving backwards between the legs of the wearer. This is otherwise a common problem in conventional sanitary towels because the leg movements of the wearer often shift the sanitary towel backwards.

In FIG. 1, an angle between a line in the longitudinal direction of the article and each of said side edges has been designated by α. The smaller the angle α, the greater the risk that the article will slide backwards in between the legs of the wearer from the point where the width of the front part element is the same as the distance between said muscle groups of the wearer. In the case of an angle of less than 30°, this risk is generally unacceptably high. An angle of preferably about 35-45° provides a good balance between secure positioning and comfort. An angle of roughly 45° has been found to be especially favourable.

An absorbent article, such as a sanitary towel, according to the invention is designed with a crotch length adapted to the anatomy of the wearer. In a sanitary towel according to the invention, use has been made of the fact that the great majority of women have a crotch length on the order of 80-100 mm. The second stiffening part element 62 has therefore been designed with a corresponding preferred crotch length G on the order of 70-120 mm, that is to say the distance from the transition area 12 to the start of the rear portion. As can be seen from FIG. 1, the distance G is measured from the space behind the first, front part element and the end of the crotch, where the second, rear stiffening element 62 divides.

Along the crotch, where the body shape of the wearer is essentially plane, the sanitary towel according to the invention is designed so as in the dry state to be relatively stiff in the lateral direction, that is to say it is sufficiently stiff not to be deformed in an uncontrolled manner in the lateral direction and form creases. As the stiffening element 6, consisting of the two part elements 61 and 62, in the embodiment described here also constitutes the major part of the absorption capacity of the sanitary towel, it is particularly desirable for it to be possible to utilize available space between the legs of the wearer in the crotch. The width of the sanitary towel in the crotch area is, with regard to the first stiffening part element 61, limited at the front by said distance between said muscle tendons directly in front of the groins of the wearer. In the backward direction from said transition area to the end of the crotch portion, the width of the second stiffening part element 62 and thus the absorbent element can increase continuously on the order of 1.5 times the width in the transition area 12 between the crotch portion and the front portion without any risk of the second stiffening part element 62 chafing the wearer in the crotch.

The above-mentioned design of the area in and around the transition area 12, that is to say the distance between the first and the second stiffening element, the design of the first part element, the size of the angle α and also the selected crotch length G on the second stiffening element 62 for the article according to the invention, affords a very good anatomical adaptation of the stiffening element, which gives the article a good fit and stability in the fitted position on the wearer. This is of particularly great importance for the functioning of the article, not least because the wetting point can, on account of the body position of the genitals of the wearer in the longitudinal direction of the crotch area, vary for different wearers. As the available space around the wetting point is very limited in width and length, optimum positioning and anchoring in this position of the first stiffening absorbent part element 61 is necessary. This is achieved by means of the design of the article described above.

The anchoring effect is consequently achieved at said muscle tendons even when the width of the first stiffening element in the area next to the transition 12 is less than the distance between said muscle tendons directly in front of the groins. The two edge portions of the first stiffening part element 61 diverge in the forward direction, and the article can slide backwards slightly until the edge portions are anchored firmly between said muscle tendons.

The first and second stiffening part elements 61 and 62 are separate from one another at the transition 12 between the front portion 1 and the crotch portion 3 of the article, which gives rise to a bending indication in the area between the stiffening part elements. The object of the article according to the invention is that the soft transition space between the first and second stiffening part elements should come to lie directly in front of said muscle tendons, in which way an article which is flexible in relation to the body is obtained at the same time as the shape and optimum positioning of the article are maintained during use of the article even under tough conditions in which the article is subjected to great stresses. Along the crotch, the body shape of the wearer is essentially plane, and the second stiffening part element 62 can therefore be essentially plane or planar and stiff in the crotch area. In the area directly in front of the groins, the body curves abruptly in relation to the crotch in prolongation thereof, and the bending indication in the form of the absence of stiffening material in the gap between the first and second stiffening elements means that the article curves adjacently to the body of the wearer. As mentioned above, the design of the article around the transition between the crotch portion and the front portion means that an article is anchored firmly between the muscle tendons in the groins of the wearer. This design results in the article virtually of necessity coming to lie in the correct place on the wearer. The folding indication which is created in the gap between the first 61 and the second stiffening part element 62 also makes a considerable contribution to the article coming to lie in the correct place on the wearer. By virtue of the fact that the first part element is separate from the second stiffening part element, a certain turning of one part element in relation to the other is permitted, which makes increased mobility possible for the wearer without annoying chafing caused by the stiffening part elements.

In the embodiment shown, the first 61 and the second part element 62 are separated from one another at said transition 12 by a distance. This distance should be at least on the order of 10 mm, and preferably on the order of 15-45 mm, in order for it to be possible, by means of said transition, to avoid said leg muscles in the groins having a negative effect on the positioning and shape of the article during its use. The presence of a transition space between the first and second absorbent stiffening part elements means that the absorbent elements can also expand into said transition space when liquid is absorbed. The space between the first and the second stiffening part elements also offers less resistance to liquid flow compared with the absorbent stiffening elements. As liquid can flow through said space and spread into the absorbent part elements from both sides of these and also through the end edge sides of said part elements, more rapid admission of bodily fluid into the absorbent part elements is achieved, which can contribute to preventing leakage in the case of heavy initial liquid flows.

The first and the second part elements can be made from the same material or from different materials. This increases the freedom to customize the article for different application requirements.

The first and the second part elements can have the same or different stiffness, which can be brought about by the selection of different material, different thickness or a different degree of compression.

The first 61 and the second part element 62 can have the same or different absorption and swelling capacity. The first part element can, for example, be non-absorbent so as to maintain its three-dimensional shape during use. This means that the front stiffening part element 61 is curved and fixed in between the muscle tendons in the groins of the wearer and adopts a bowl-like shape.

The first and the second part element can be connected by an elastic element (not shown). This makes it possible for the first and the second part element to return to their intended relative position after turning or pulling-apart of the two part elements during use of the article.

According to one embodiment, at least the second of said stiffening part elements is absorbent and at the same time constitutes the absorbent element. It swells during absorption while on the whole retaining its geometry in the transverse direction of the article.

According to an especially preferred embodiment, at least the second 62 of said stiffening part elements is absorbent and at the same time constitutes the absorbent element, which swells during absorption while retaining its geometry in the transverse direction of the article.

The second stiffening part element 62 and therefore the absorption element also extend part of the way in over the rear portion 2 of the article. In the rear portion, the stiffening part element 62 has a cutout 13 extending from its end edge in the direction towards the crotch portion, as a result of which the article can fold along a longitudinal line L in the cutout and as a result of which the stiffening part element 62 forms legs 14 and 15 which are located on both sides of the cutout and are more flexible than the wider crotch portion. The legs 14 and 15 can be made vertically movable in relation to one another by virtue of the width selected for the cutout. This cutout 13 is thus very useful for obtaining the desired adaptation and flexibility of the article in relation to the body. The fold formed in the cutout during use of the article can penetrate the cleft between the buttocks of the wearer and in this way provides very good protection against leakage via the cleft between the buttocks, which type of leakage usually occurs during the use of conventional products when the wearer is lying on her back. The cutout 13 also makes it possible for said legs 14, 15 of the stiffening element to be displaced vertically in relation to one another when various body movements take place, for example when the wearer is walking.

In the illustrative embodiment shown in FIG. 1, the cutout 13 is wedge-shaped and located symmetrically in relation to the longitudinal symmetry line L of the article and also forms an angle $\beta$ on the order of 20°. This angle can vary within wide limits but of course depends on the design of the rear portion 2. When the rear portion is of considerably wider design, as in the embodiment according to FIG. 5, said angle $\beta$ can vary between the order of 10° and 120°, preferably between 15° and 40°.

In the illustrative embodiment shown, the stiffening part element 62 (and if appropriate the stiffening part element 61) also serves as the main absorption element of the article and has very great liquid-spreading capacity for rapid spreading of bodily fluid received from the wearer in the narrow crotch area directly in front of the genitals of the wearer over the absorbent portions of the whole article, that is to say over the entire stiffening and also liquid-absorbing part element 62 and also, if appropriate, the part element 61. The stiffening absorbent part element 62 is designed so as to swell in the depth direction during absorption and on the whole retain its geometry in the transverse direction of the article, which results in the stiffening element retaining its fit and secure positioning in relation to the body of the wearer throughout use of the article. The absorbent stiffening element 62 has great swelling capacity in the depth direction and attendant great absorption capacity. If the same material is selected for the part element 61, it will of course have the same properties.

According to one embodiment, the stiffening absorbent part elements 61 and 62 are made of a dry-formed fibre mat with a density preferably between 0.15 and 0.75 g/cm$^3$ and a weight per unit area on the order of 100-400 g/m$^2$. A dry-formed fibrous mass in the form of a fibre mat is described in U.S. Pat. No. 5,730,737. The fibre mat produced is very stiff after forming and compression. The fibre mat can be used as it is or be mechanically softened to the desired stiffness.

A way of very accurately forming fibrous webs for use as absorption elements in absorbent articles is described in Swedish patent application 0101393-7. The fibrous webs are formed by air-laying fibres, separate air flows containing fibres being fed to a number "n" of different mat-forming wheels, where "n" is a whole number which is at least 2. Separate web layers are formed on the individual web-forming wheels. The fibrous web is formed by said web layers being combined to form a common fibrous web downstream of the mat-forming wheels, which web has very great manufacturing accuracy by virtue of the manufacturing method.

The manufacturing speed and thus the web speed can be very high, and the desired manufacturing accuracy at the web speed concerned is achieved by selecting a sufficiently high number "n" of mat-forming wheels. By virtue of this manufacturing method, very thin fibrous webs can be manufactured with very great accuracy.

The fibre mat for forming the stiffening absorbent part elements 61 and 62 can be made of a mixture of cellulose fibres and viscose fibres, the presence of the latter giving the fibre mat a greater wet strength than a fibre mat made of only cellulose fibres. The fibre mat for forming the stiffening absorbent part elements can also contain synthetic melt fibres, by means of which the strength of the fibre mat can be increased by heat treatment to melt said synthetic melt fibres.

The absorbent stiffening elements can also be formed from foamed material.

A further example of stiffening absorbent material is a laminate in the form of one or more plies of tissue and superabsorbent material (SAPs). The material or combination of different materials serving as an absorbent element and also, if appropriate, as a stiffening element can contain SAPs in the form of fibres, particles or foam.

The selection of compression pattern also makes it possible to vary the extensibility of the fibre mat. The dry-formed fibre mat can be provided with the desired reduced stiffness and the desired extensibility by virtue of the degree of compression selected and the compression pattern selected.

Furthermore, it is possible to pattern-compress only specific zones for the purpose of providing only these zones with an extensibility and stiffness which are different from the rest of the stiffening absorption part elements. In the same way, the stiffening absorption part elements 61 and 62 can be compressed over their entire extent but with different patterns in different zones. By virtue of the presence of stiffening absorption part elements which can in a simple manner, by virtue of the pattern compression selected, be provided with the desired stiffness and the desired extension in different zones, and in which the stiffness and extension properties can be selected essentially freely in these zones, the present invention has brought about a new and previously unknown way of controlling and guiding the shaping of an absorbent article intended for taking up bodily fluids.

As mentioned above, the stiffening absorbent part element 62 (and if appropriate the part element 61) has great swelling capacity in the depth direction, which has been achieved by great compression of the materials forming the part elements in connection with their production.

In the dry state, the material formed, such as the fibre mat, is hard-compressed and stiff, which affords the shaped and anatomically adapted absorption and also stiffening element as a whole, that is to say the element 6 formed by the part elements 61 and 62, very good stability in the fitted position on the wearer and very great spreading capacity, as a result of which the total absorption capacity of the absorption element can be optimally utilized and leakage caused by local oversaturation can to a great extent be eliminated. During absorption of liquid, the absorption body of the part elements swells in the depth direction but the absorption elements do of course swell slightly in other directions as well. When the anatomically adapted stiffening absorption element swells, further improved anatomical adaptation is in fact achieved, which contributes to the stability and flexibility of the article in relation to the body shape of the wearer when the stiffness of the part elements decreases during absorption and attendant swelling.

So as to function in the desired manner, the stiffening part elements have a preferred stiffness in the dry state on the order of 1-15 N measured according to ASTM D 4032-82. This "Circular Bend Procedure" is described in detail in EP 336 578.

The stiffening absorbent part elements 61 and 62 can also be made of laminates of a number of non-woven fabric layers or tissue layers which are fixed to one another for increased stiffness and which can have highly absorbent particles between individual plies. The individual plies can be fixed to one another by a bonding agent, such as adhesive or melt fibres. The highly absorbent particles can also contribute to bonding. The stiffness is controlled by virtue of the selection of the number of plies and the quantity of bonding agent included and the selection of highly absorbent material and how the adhesive capacity thereof is utilized.

A stiffening absorbent part element of this type can also be provided with different stiffness and different extensibility in different zones of the extent of the part element. These properties can in this case as well be controlled by means of compression patterns. This compression can be combined with the supply of heat, which supply can vary in different zones. Furthermore, bonding agent can be applied in different patterns to control the shaping of the stiffening absorption part elements during use. A varying supply of moisture in different areas in connection with compression is another parameter for controlling the shaping of the article during use.

Another example of the construction of a unit serving as both absorption element and stiffening element is a number of layers of LDA, that is to say layers of the same type as in the drainage and insulating layer 7. However, the bonding of the layers of LDA in the stiffening absorption part elements is much harder both within and between individual layers. This bonding is brought about by hard-compression of the LDA layers and suitably by using both melt fibres and latex, what is known as the multibond technique. In this design as well, stiffness and extensibility can be controlled by compression pattern selection and also by variation of the heat supply in different zones.

Further material examples are mixtures of LDA and HDA (high density airlaid) if appropriate in combination with other material layers, such as tissue.

Pattern compression can be used in all the material examples described above, and it is then possible to achieve, for example, hinge effects along compression lines or compression zones.

Pattern formation can take place in connection with compression of stiffening absorption elements. Alternatively, pattern compression can take place in a separate step after smooth compression. Use can be made of, for example, a web of material made in one of the ways described above and smooth-compressed as the starting material for stiffening absorption part elements, which is pattern-compressed in the desired manner and depending on the type and size of article to be manufactured. After pattern-compression, individual products are cut out. Pattern-compression and cutting-out of separate stiffening absorption part elements can take place in a single step in a combined cutting and pattern-compression unit.

As described above, stiffening part elements can also constitute the main absorption element of the article. This is particularly suitable from the point of view of production because there are fewer elements to handle than if, for example, stiffening part elements and the absorption element constitute separate elements.

The invention also includes designs in which the stiffening part elements are separate from the main absorption element of the article. The stiffening part elements can then be absorbent or non-absorbent. The main purpose in such a design is to constitute a stiffening shaping element.

In addition to the interpretation of the term stiffening element as constituting a completely separate element or constituting both the main absorption element and the stiffening element of the article, the term can also embrace the interpretation that all the material plies, bonding agents etc. included in the article in the area of the desired stiffening together form the desired stiffening element. For example, a unit serving as a stiffening element and also as an absorption element, with the dimensions indicated above and with the geometry described above but with stiffness which is in itself inadequate, is included in the invention if the necessary stiffness is obtained by being bonded together with other material plies in the area of the stiffening element.

The embodiment shown in FIGS. 3 and 4 differs from the embodiment shown in FIGS. 1 and 2 only in that an elastic means 16 is arranged in a pretensioned state in the longitudinal direction of the article and centrally along the rear portion 2 of the article. The same reference numbers have been used in FIGS. 3 and 4 as in the embodiment according to FIGS. 1 and 2.

The elastic means 16 is arranged centrally in the cutout and extends in the rear portion slightly beyond the ends of the legs 14 and 15 and, in the other direction, part of the way in over the crotch portion. The elastic means is arranged on the inside or on the outside of the liquid-tight outer layer and is connected to the latter and/or other layers forming part of the article. The extent of the elastic means is not critical but can vary somewhat in relation to the illustrative embodiment shown in FIG. 3. One purpose of the elastic means 16 is, during use of the article, to draw adjacent material portions together and contribute to curving the article in the upward direction towards the body of the wearer for better contact with the body. Another purpose is also to initiate and form the fold 17 which, during use of the article, is intended to penetrate part of the way into the cleft between the buttocks of the wearer and prevent leakage of bodily fluid backwards along the cleft between the buttocks, which leakage can otherwise occur when the wearer is lying on her back.

Figure 5:
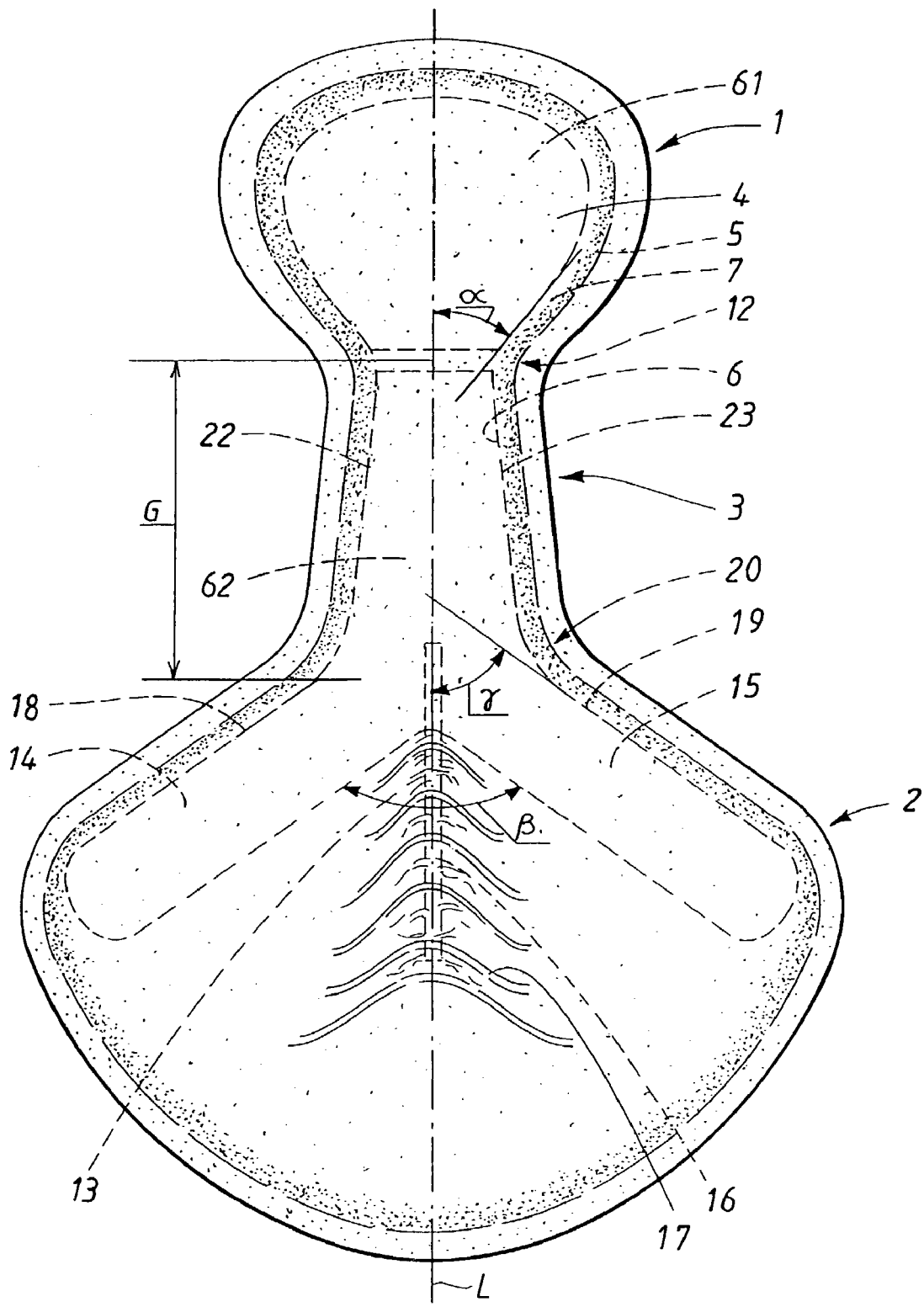
FIG. 5 shows a plan view of a third embodiment of the article according to the invention.

In the embodiment shown in FIG. 5, the components which correspond to similar parts in the embodiments according to FIGS. 1-4 have been provided with the same reference numbers. The article in the embodiment according to FIG. 5 is provided with a considerably wider rear portion 2. The article also differs from the embodiments described above in that there are no wings for attachment around the crotch portion of the briefs of the wearer.

The second stiffening part element 62 extends with its leg portions 14, 15 in over the rear portion 2. The outer side edges 18, 19 of the second stiffening part element 62 on the legs 14, 15 diverge from the crotch portion in over the rear portion. In a rear transition area 20 between the crotch portion 3 and the rear portion 2, said outer edge sides 18, 19 abruptly change direction in relation to the edge sides 22, 23 of the stiffening part element 62 in the crotch portion of the article.

The purpose of the edge sides 18, 19 of the second part element 62 diverging in the backward direction on the rear portion 2 is that the article, in addition to being anchored firmly at the transition 12 between the front portion and the crotch portion, will also be anchored at the rear in the transition area between the crotch portion 3 and the rear portion 2, as a result of which the article is very stable and well fixed on the wearer during use at the same time as it feels comfortable for the wearer by virtue of its anatomical adaptation in terms of shape, size and geometry. In the drawing, an angle between the longitudinal direction of the article and each outer edge side 18, 19 has been designated by $\gamma$. For a good anchoring function, this angle preferably should not be less than roughly 30°. Furthermore, so as not to feel uncomfortable, the angle preferably should not exceed roughly 60°.

The distance G between the transition areas 12 and 20 is adapted to the crotch length of a wearer and, as mentioned above in connection with the embodiments according to FIGS. 1-4, this distance G is suitably on the order of 70-120 mm. As mentioned above, the essentially plane area of the crotch of women directly in front of the genitals has a length on the order of 80-100 mm, that is to say all women are essentially the same size in this plane area. It has been found that having a crotch dimension G on the article on the order of 70-120 mm functions well for most wearers. The larger the angles a and y and the stiffer the stiffening element, the more important it is that the crotch dimension on the article corresponds to the length of the plane crotch portion of the intended wearer directly in front of her genitals if the article is not to feel uncomfortable.

It may therefore be suitable to have a range of sizes of the article according to the invention depending on the selection of stiffness and said angles, so that different wearers can find a suitable size with regard to dimensions and angles. This of course applies to all the embodiments of the invention described here but is particularly important when the article is intended to be anchored both at the front and at the rear. The requirement for size adaptation also increases for all the embodiments the stiffer the absorbent part elements 61 and 62 are.

The stiffening part element which is at the same time the absorption element 62 in the embodiment according to FIG. 5 has a cutout 13. As in other illustrative embodiments described above, this is wedge-shaped but has a larger angle $\beta$ which, in FIG. 5, is obtuse. The angle $\beta$ can vary within wide limits between of the order of 10° and 120°. How large a cutout 13 is required depends on the function required of the legs 14 and 15 and the absorption capacity required in the rear portion 2 of the article.

The smaller the angle $\beta$, with the same width of the rear portion in its entirety and with the same angle $\gamma$, the wider are the legs 14, 15, which in turn results in increased absorption capacity and increased stiffness in the rear portion.

The size of the cutout also influences the height of the fold 17. This fold height and also the shaping of the rear piece 2 also depends on the pretensioning and the extent of the elastic means 16.

The illustrative embodiment of the article according to the invention shown in FIG. 5 can serve as, for example, a night towel. Like other embodiments, this embodiment is also suitable as an incontinence pad. This type of protection should be capable of rapidly receiving large quantities of liquid discharged at a high flow rate from the wearer.

An article of the type shown in FIG. 5 can, in combination with supporting pants or with special elastic pants adapted for supporting the article, serve as a nappy for receiving both urine and motions. If the article is to serve as a nappy, the cutout 13 should be relatively large, corresponding on the whole to that shown in FIG. 5, in order for it to be possible for discharged motions to be taken up in the cutout 13 of the rear portion.

FIGS. 6-9 show a further embodiment of an article according to the invention. This embodiment corresponds in many respects to the embodiments according to FIGS. 1-4, and those parts corresponding to the same parts in the embodiments described above have been provided with the same reference numbers in the drawing.

A way of reducing further the risk of edge leakage caused by the sanitary towel being deformed during use, in addition to the arrangement of the stiffening part elements 61 and 62, is to provide the sanitary towel with a raised portion, what is known as a hump, which raised portion has been designated by reference number 240. The raised portion or hump is intended to make contact with the genitals of the wearer during use of the sanitary towel. Discharged bodily fluid can in this way be caught as soon as it leaves the body of the wearer and be absorbed immediately into the article instead of running out over the surface of the latter.

Figure 7:
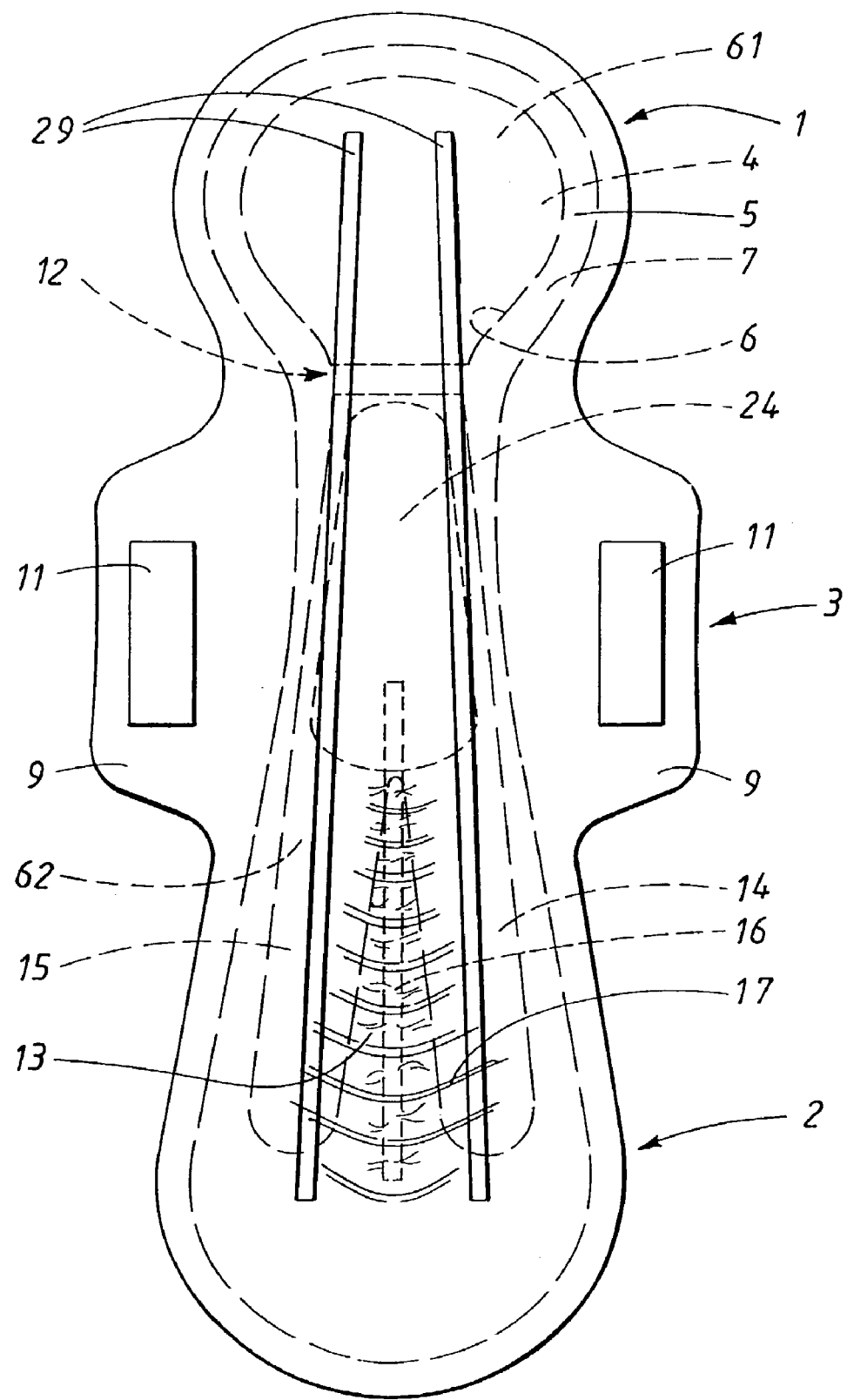
FIG. 7 shows a plan view of the article according to FIG. 6 from the opposite side.
Figure 8:
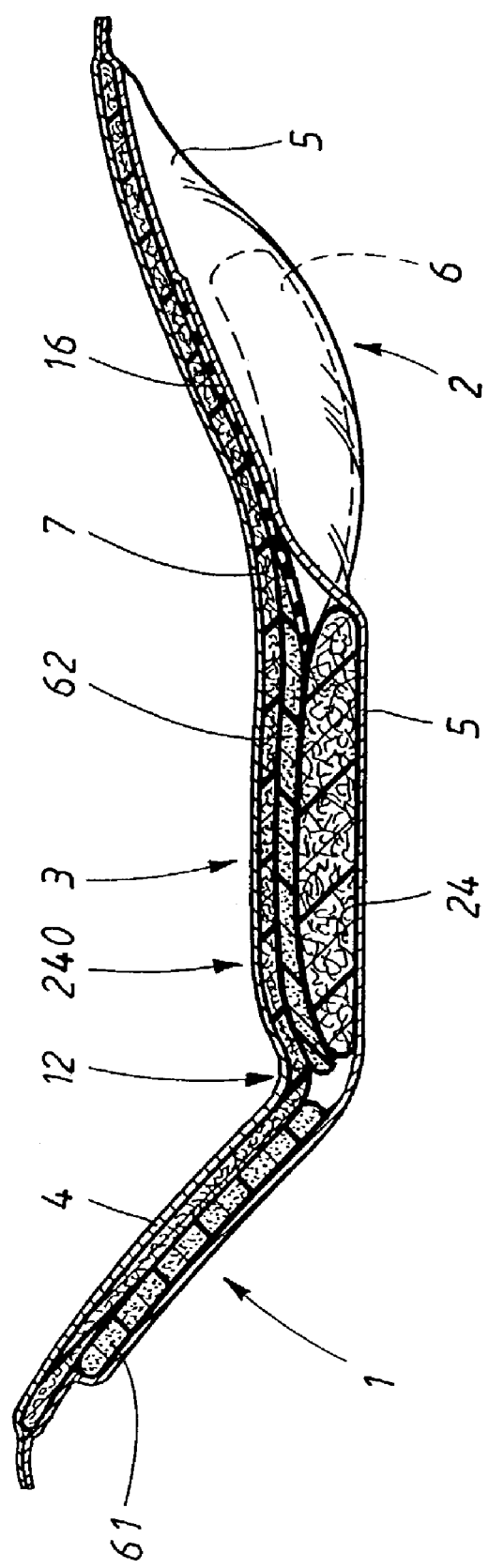
FIG. 8 shows a section along the line VIII-VIII in FIG. 6 but in a curved utilization state.

In the embodiment shown in FIGS. 6-9, the hump is brought about by a hump-forming element 24 which, as can be seen most clearly from FIG. 8, is arranged below the second stiffening part element 62 inside the liquid-impermeable outer layer 5. The positioning of the hump-forming element results in a number of advantages. Admission of bodily fluid is not interfered with by hump material in direct proximity to the genitals of the wearer, but the parts located closest to the genitals of the wearer can be optimized with regard to admission and absorption capacity.

The positioning selected for the hump-forming element below the stiffening part element 62 in combination with the positioning along the crotch portion of the article also contributes to the article curving and shaping itself in the desired manner when fitted on the wearer. At the transition 12 between the crotch portion 3 and the front portion, as can be seen from FIG. 9, a point of inflection 27 is formed, in front of which, that is to say in the front portion of the article, the article is concave at least over a portion next to said transition 12. Behind said point of inflection, that is to say along the crotch portion of the article, the article is, in the area directly in front of the hump-forming element 24, convex, that is to say the stiffening part element 62 is curved in this area, upwards in the crotch portion 3, as can be seen most clearly from FIGS. 8 and 9. In addition to bringing about the raised portion 240 on the front side of the article, the hump-forming element makes it possible to guide the stiffening element in the desired direction of curvature at different points of the extent of the stiffening element.

The hump-forming element 24 is made of, for example, a non-absorbent synthetic wadding which has resilient properties. Such a hump-forming element retains its shape and function even when the material is in a wet state.

The hump-forming element can also consist of a foamed material, for example polyurethane foam or the like.

As the hump-forming material is, in the embodiment shown, located below the absorbent part element 62, which also serves as the stiffening element, the hump-forming material can be liquid-absorbing. In such a design, it is suitable to select a material which has larger capillaries than the absorption element has, so that liquid can be transported to the hump-forming material only when the absorption element is saturated with liquid. A hump-forming absorbent fibrous layer which has resilient properties only in the dry state can therefore also be used in such a construction because the material is essentially dry until the absorption element itself is saturated with liquid. The positioning of the hump-forming element 24 below both the stiffening and the absorbent part element 62 therefore affords a number of important advantages.

The element forming the raised portion 240 has an elongate shape and extends over the entire crotch portion in the illustrative embodiment shown. The length of the raised portion can preferably vary between roughly 20 mm and 120 mm.

The element 24 forming the raised portion is narrower than the rest of the article in the crotch area. In this way, it is made possible for laterally surrounding portions 25, 26 of the rest of the article to shape themselves around the element 24 forming the raised portion. The material forming the raised portion is suitably at least twice as thick as the surrounding areas 25, 26.

In FIG. 8, the article has been shown in curved, three-dimensional form for the sake of clarity. An absorbent article of the type described here is of course always three-dimensional in the conventional sense, that is to say it has length, width and thickness.

In this context, however, the term three-dimensional means that the article must be curved in some way to adapt to the body shape of the wearer.

FIG. 8 shows that the first 61 and the second part element 62 are arranged at a distance from one another in the transition area 12, which results in a folding indication being created in this area.

In this context, the term plane form or plane state means that the article is essentially plane or planar. The article shown in FIGS. 6 and 7 is essentially plane according to this definition in spite of the fact that the elastic means draws the material layers together in the cutout 13 between the legs 14, 15.

Figure 6:
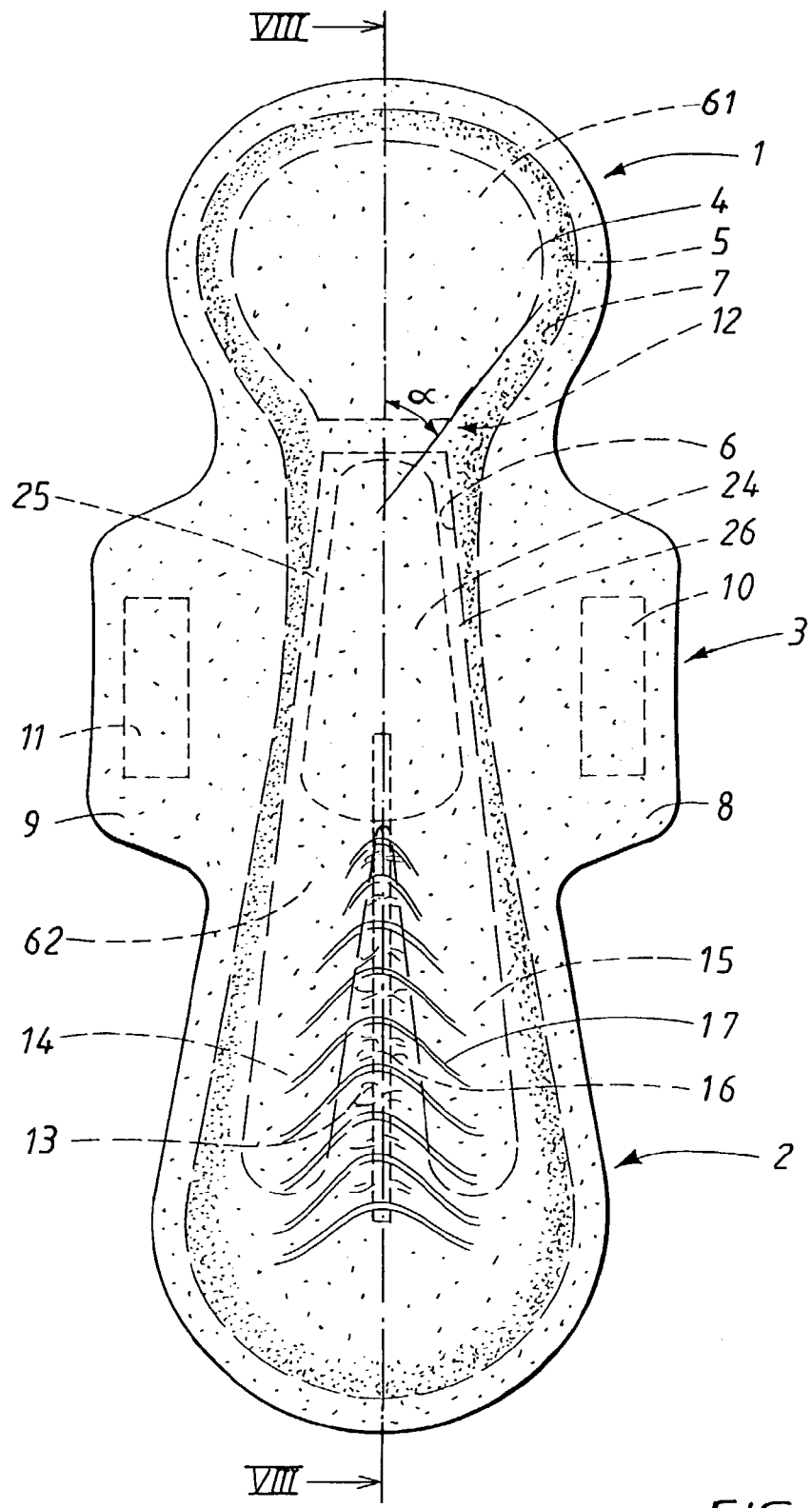
FIG. 6 shows a plan view of a fourth embodiment of the article according to the invention seen from that surface of the article which receives bodily fluids.
Figure 9:
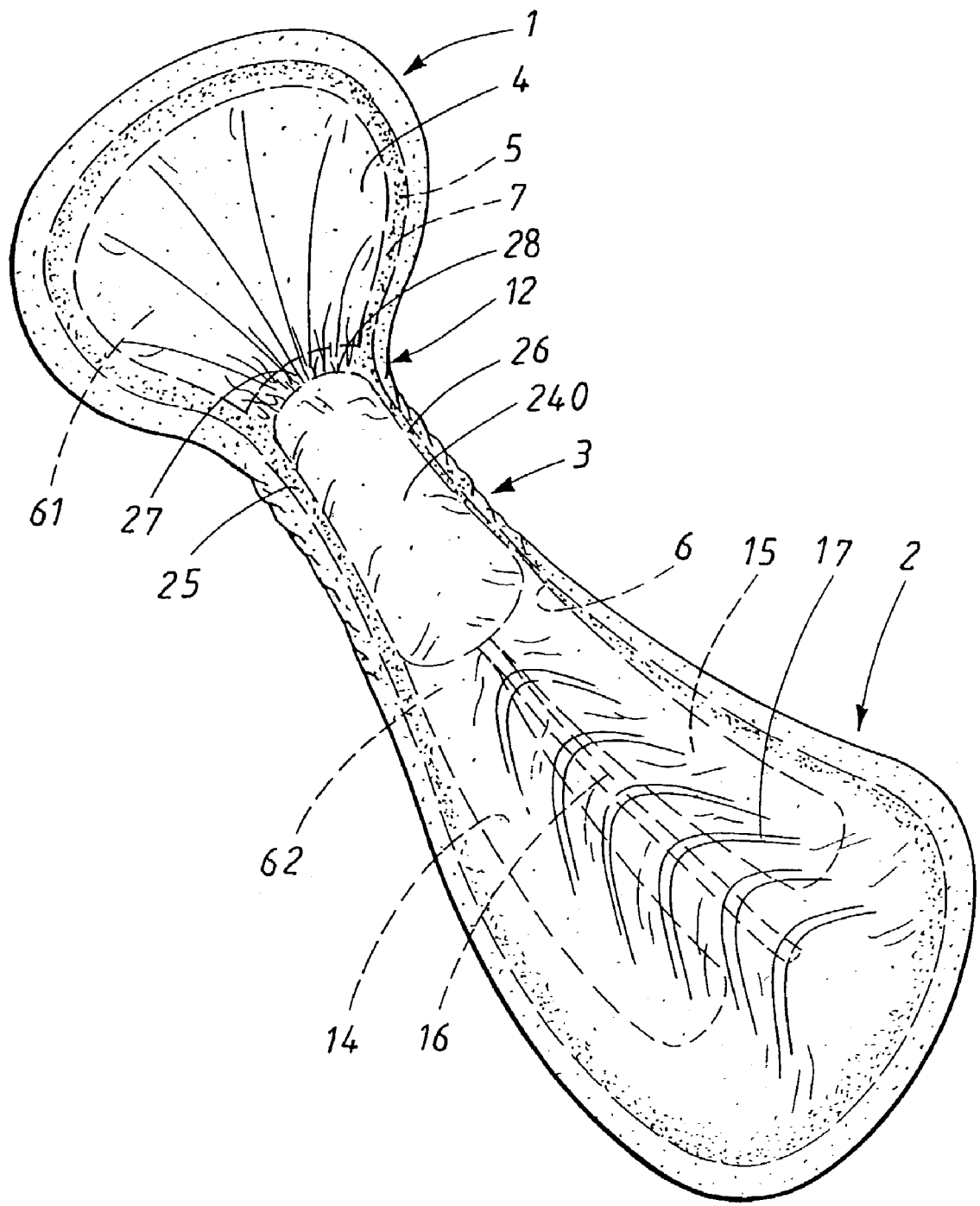
FIG. 9 shows, in perspective and in a utilization state, the article according to the fourth embodiment and also the embodiment shown in FIGS. 6-8.

Articles in plane form according to FIGS. 6 and 7 can be packed simply, for example in stacks in a box or bag and yet, when put on, be made to adopt an anatomically adapted three-dimensional shape, as shown in FIGS. 8 and 9, without any measures whatsoever.

By virtue of its special design with said transition space, which is intended to be arranged directly in front of said muscle tendons during use of the article, the hump-shaped element 24, the action of the elastic means 16 and the stiffness and geometric shape of the stiffening part elements 61, 62, the article is anatomically adapted and predestined to adopt during handling a three-dimensional shape according to FIGS. 8 and 9 adapted to the body shape of the wearer.

In the illustrative embodiment shown, the stiffening and also absorbent part elements 61 and 62 have the same stiffness properties over their entire extent. As a result, uncontrolled creases, which could give rise to uncontrolled and unintentional liquid flow, do not normally arise over the extent of the stiffening part elements.

At the transition 12 between the crotch portion 3 and the front portion 1, curvature is initiated because the article as a whole changes its flexural resistance here, mainly by virtue of the presence of a distance between the first 61 and the second part element 62. The flexural resistance in this area is also influenced by the hump-forming element having its end around this transition and also to some extent by the stiffening part elements 61 and 62 being narrowest here with a dimension M adapted to the distance between said muscle tendons of the wearer. At this transition 12, a point of inflection 27 is formed, in front of which the article is concave and bowl-shaped, whereas it adopts a convex shape behind this point of inflection 27. In the embodiment according to FIG. 9, the hump-forming element is rounded at the front along a line 28.

In this way, the stiffening element is caused by this rounded line to adopt an evenly rounded bowl shape in the front portion, as can be seen from FIG. 9.

In the transition area 20 between the crotch portion 3 and the rear portion 2 as well, the hump-forming element 24, which in the embodiment shown extends as far as said transition area 20, is rounded at its rear end. As a result, no undesirable creases arise, but the transition between the convex crotch portion and the two side portions of the rear portion 2 sloping downwards around the fold 17 formed by the elastic means 16 is even and smooth without undesirable creases.

The raised portion 240 formed by the hump-forming element 24 also has the advantage that the fold extending into the cleft between the buttocks of the wearer does not extend in too abruptly or too far and give rise to chafing. In this respect also, the hump provides a soft transition in the transition area between the crotch portion and the rear portion.

In all the embodiments described above, it is suitable for the article to be provided with a pressure-sensitive adhesive on the outside of its liquid-impermeable outer layer 5. This has been indicated in FIG. 7 by adhesive strands 29 which, before use of the article, are covered in a conventional manner by a cover strip 30 treated with release agent. Although the article according to the invention is anatomically adapted, it is suitable, for reliable secure positioning, to have a pressure-sensitive adhesive on the liquid-impermeable outside of the article for interaction with the briefs of the wearer, which contributes to keeping the article in the intended position on the wearer. The selection of suitable attachment, that is to say whether and to what extent pressure-sensitive adhesive for attachment to the briefs of the wearer is to be used, is guided by the selection of the stiffness of the stiffening element included.

According to an embodiment (not shown in the drawing), the article can be attached to or interact with the body of the wearer by means of adhesive or friction coating. The friction means or adhesive can be the only means of attachment, but it can also be used in combination with pressure-sensitive adhesive intended for attachment to the briefs of the wearer.

Figure 10:
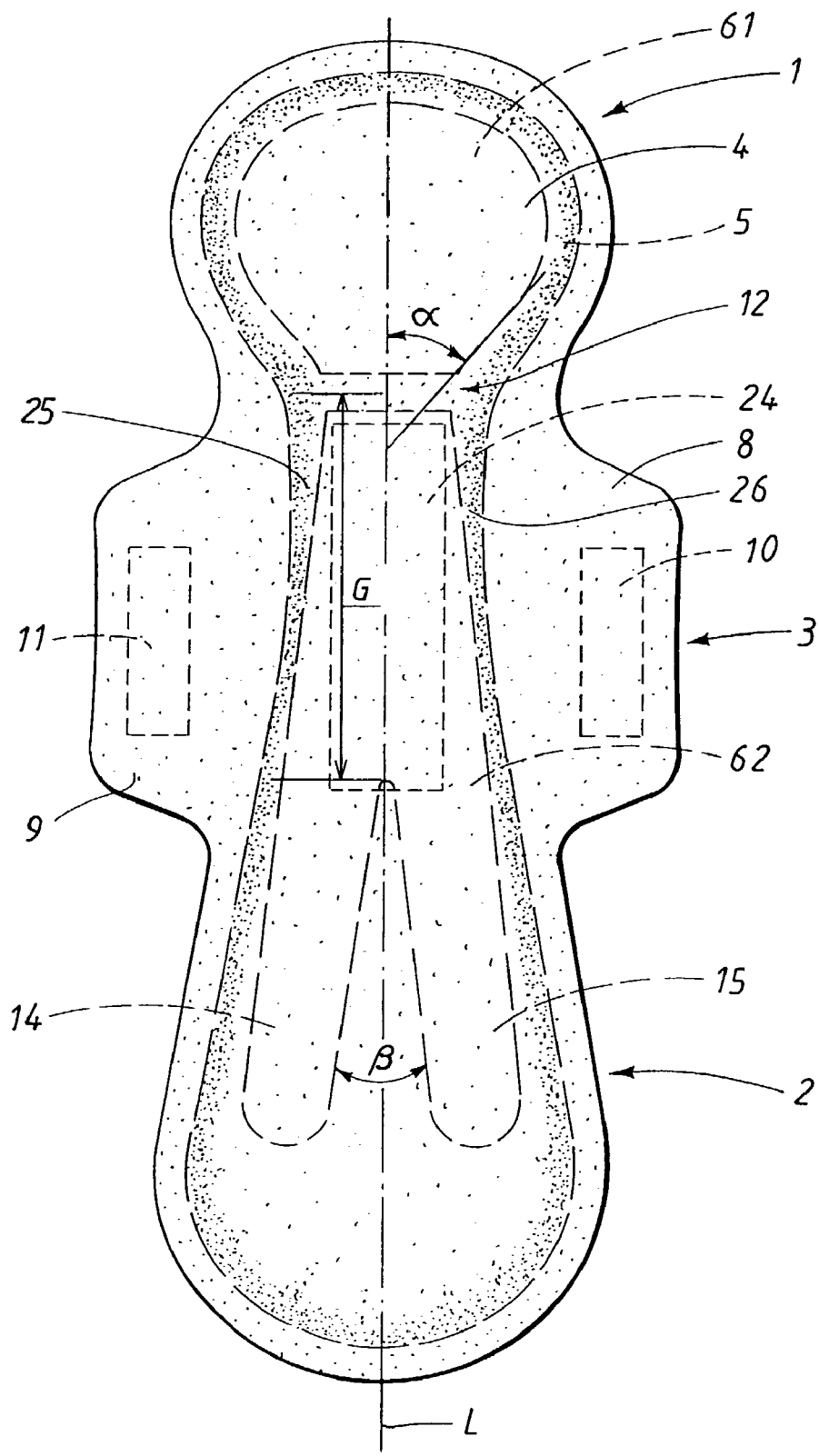
FIG. 10 shows a plan view of a fifth embodiment which is slightly simplified in relation to the embodiment according to FIGS. 6-9.

FIG. 10 shows an embodiment which is modified slightly in relation to the embodiment according to FIGS. 6-9. Those parts in the article according to FIG. 10 corresponding to similar components in the embodiment according to FIGS. 6-9 have been provided with the same reference numbers.

The article shown in FIG. 10 is simpler in terms of manufacture than the embodiment according to FIGS. 6-9. The article according to FIG. 10 has no longitudinal elastic in the cutout 13 between the legs 14 and 15 of the stiffening part element 62.

During use of an article according to FIG. 10, the rear portion 2 is folded along the line L in spite of the absence of the elastic means. In this case also, a stiffening of the rear portion is therefore obtained after folding of the rear portion along the line L. The flexural rigidity increases after the article has been folded along the line L, which results in the rear portion of the article being more stable. During use of the article, the fold formed along the line L will penetrate part of the way into the cleft between the buttocks of the wearer and thus contribute to the article staying in place in the lateral direction at the same time as the fold catches any bodily fluid which runs in the cleft between the buttocks of the wearer.

The article according to FIG. 10 also differs from the embodiment according to FIGS. 6-9 in that the hump-forming element 24 has straight end edge sides and also the same width along its entire length. The hump-forming element is suitably of such a thickness that, directly in front of the raised portion 240, the article is at least twice as thick as the surrounding areas 25, 26.

Even when the end edge sides are straight, the article will during use essentially shape itself as described with reference to FIGS. 8 and 9 above, that is to say an inflection point is formed at the transition 12 between the front portion and the crotch portion. In front of the inflection point, the article is concave and bowl-shaped while, behind this inflection point, it adopts a convex shape. With the embodiment according to FIG. 10 also, the bowl shape is evenly rounded and has no annoying creases.

Annoying creases do not arise in the transition area between the crotch portion and the rear portion either, but the article according to FIG. 10 will in this area as well shape itself in essentially the same way as described above in connection with the embodiment according to FIGS. 6-9.

Figure 11:
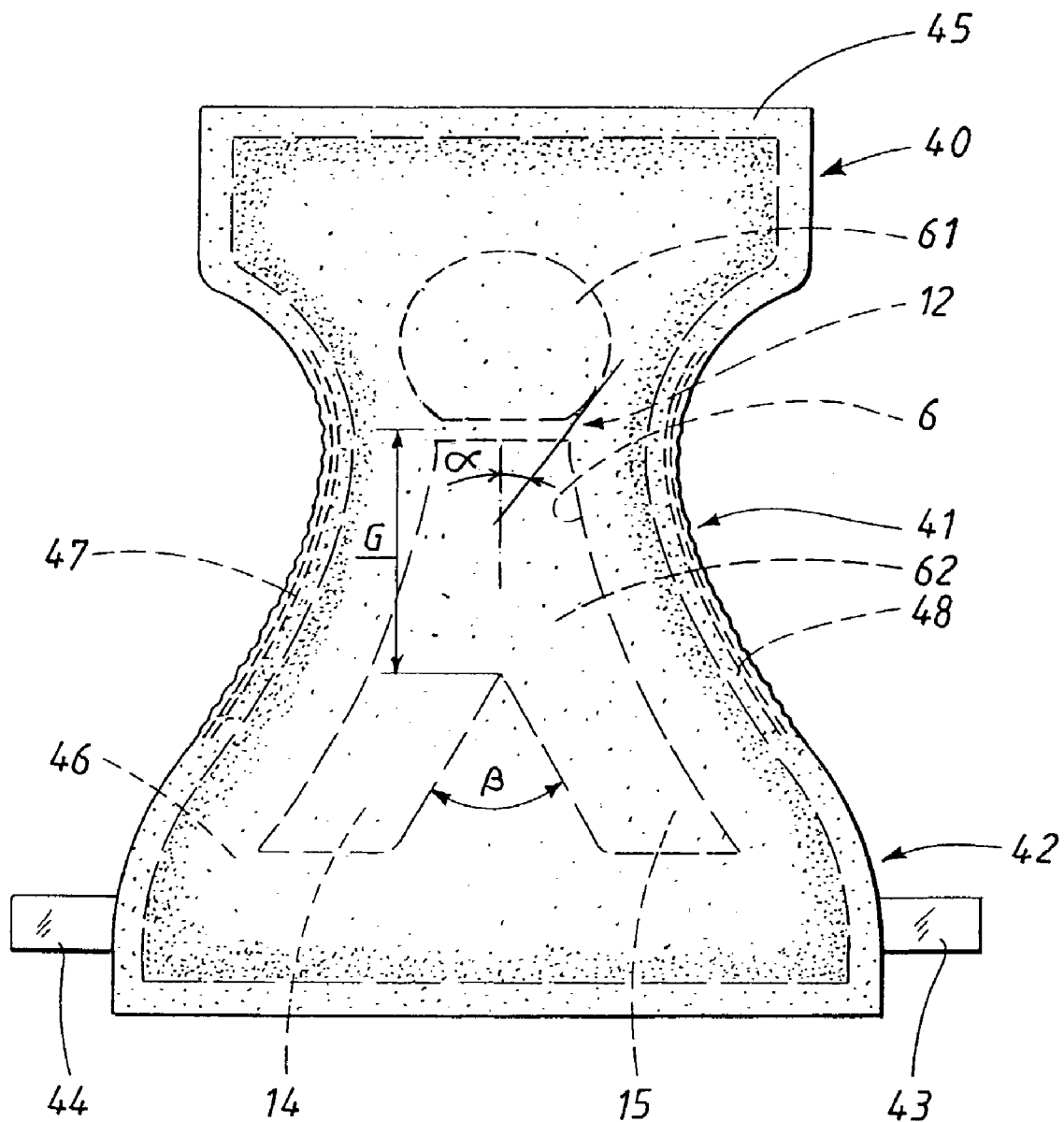
FIG. 11 shows a plan view of an absorbent article according to the invention in the form of a nappy.

FIG. 11 shows an embodiment in the form of a nappy. This has a front portion 40, a crotch portion 41 and a rear portion 42. Outwardly, the embodiment shown of an article in the form of a nappy according to the present invention is of conventional design. When the nappy is put on, the front portion 40 and the rear portion 42 are intended to be fitted around the waist of the wearer and to be closed in the fitted position by means of tape flaps 43, 44. In FIG. 11, the nappy is shown diagrammatically in plane form from the inside and is provided with a covering in the form of a liquid-permeable inner layer 45, suitably made of nonwoven fabric, and an outer layer made of thin plastic film (not shown), suitably made of polyethylene. Inside the inner layer, an essentially hourglass-shaped absorption layer 46 is indicated, which is thin and very flexible. In the crotch portion, leg elastic 47, 48, which is intended to fit tightly around the thighs of the wearer during use of the nappy, has been arranged along the edge portion.

FIG. 11 shows diagrammatically stiffening and also absorbent part elements 61 and 62 of the same type as described in the illustrative embodiments described above. In FIG. 11, components corresponding to similar parts in illustrative embodiments described above have been provided with the same reference numbers. The stiffening absorbent elements are anatomically adapted in the same way as in illustrative embodiments described above.

As mentioned above, a person has essentially the same dimension between said muscle tendons throughout his or her life. Nappies according to FIG. 11 therefore function in principle for both children and adults if the nappy as a whole is adapted in terms of size.

A nappy according to the invention of the type shown in FIG. 11 has a superior fit compared with conventional nappies. The presence of the stiffening part elements means that, when the nappy is put on, it is guided into the correct position on the wearer and that it remains in this position during use of the article.

In all the illustrative embodiments described above, the width of the stiffening and also absorbent part element 62 increases continuously from the transition 12 between the front portion 1 and the crotch portion 3 to the transition area 20 between the crotch portion 3 and the rear portion. One reason for this is that the available space between the legs of the wearer is very limited, and it is important to make optimum use of the width of this area. The width can increase by of the order of 1.5 times between the transition 12 and the transition area 20 without this feeling uncomfortable for the wearer. Another reason is that the article lies more stably on the wearer when the stiffening part element 62 is made as wide as possible along the crotch portion.

Figure 12:
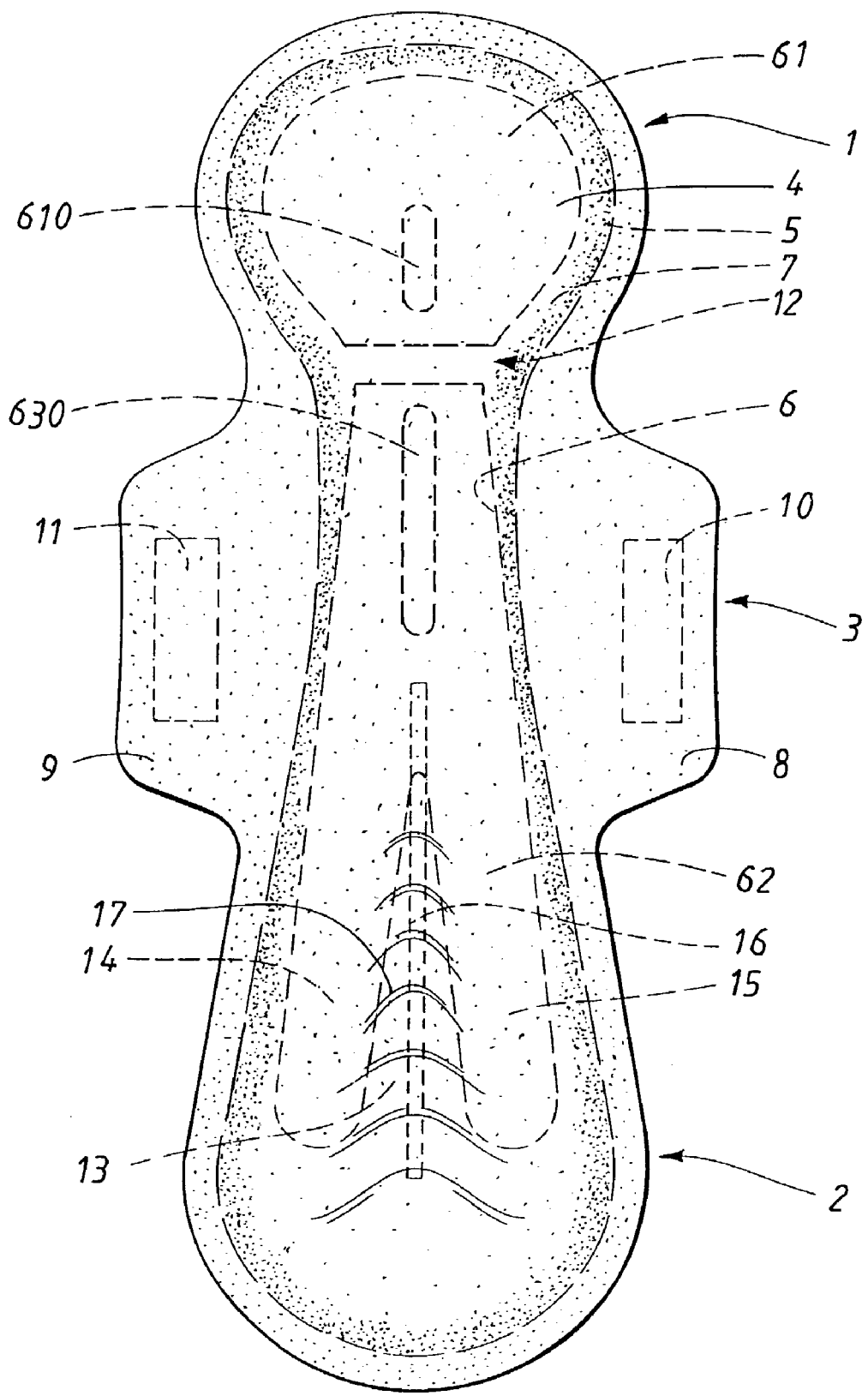
FIG. 12 shows a plan view of a further embodiment of the article according to the invention, seen towards that surface of the article which receives bodily fluids.

FIG. 12 shows a further embodiment which is modified in relation to the embodiment according to FIG. 3. Those parts in the article according to FIG. 12 corresponding to similar components in the embodiment according to FIG. 3 have been provided with the same reference numbers.

The stiffening and also absorbent element 6 includes a first part element 61 and a second part element 62 which are separated from one another by such a distance in the longitudinal direction as will create the space necessary for the article according to the invention for the muscle tendons of the wearer on both sides of the crotch of the wearer in the groin of the latter.

In the embodiment according to FIG. 12, the first stiffening part element 61 has a first through-hole 610 which is oblong and extends in the longitudinal direction of the article and along the centre line of the article. This hole 610 makes possible resilient compression in the lateral direction of the first part element when lateral forces act against the side edges of the first part element. The stiffness and resilience of the first stiffening part element 61 with regard to stresses in the lateral direction of the first part element can therefore be controlled on the one hand by the stiffness of the material itself, which is selected by way of material, construction and compression selected, and on the other hand by selection of the size and shape of the hole 610.

In the embodiment shown in FIG. 12, the second part element 62 is also provided, in the crotch portion, with an elongate second through-hole 630 along the longitudinal centre line of the article, which second hole makes possible resilient compression in the lateral direction of the second part element in the crotch area of the article when lateral forces act against the crotch portion during use of the article. The stiffness and resilience of the article in the crotch area can be controlled by way of the shape and extent selected for the second hole. This stiffness and resilience also depends of course on the stiffness of the material itself, as described above in connection with the description of the first part element 61 with the hole 610. The arrangement of the holes 610 and 630 therefore affords a further possibility for controlling the stiffness properties and resilient properties of the article in the lateral direction in addition to the stiffness of the constituent layers.

Figure 13:
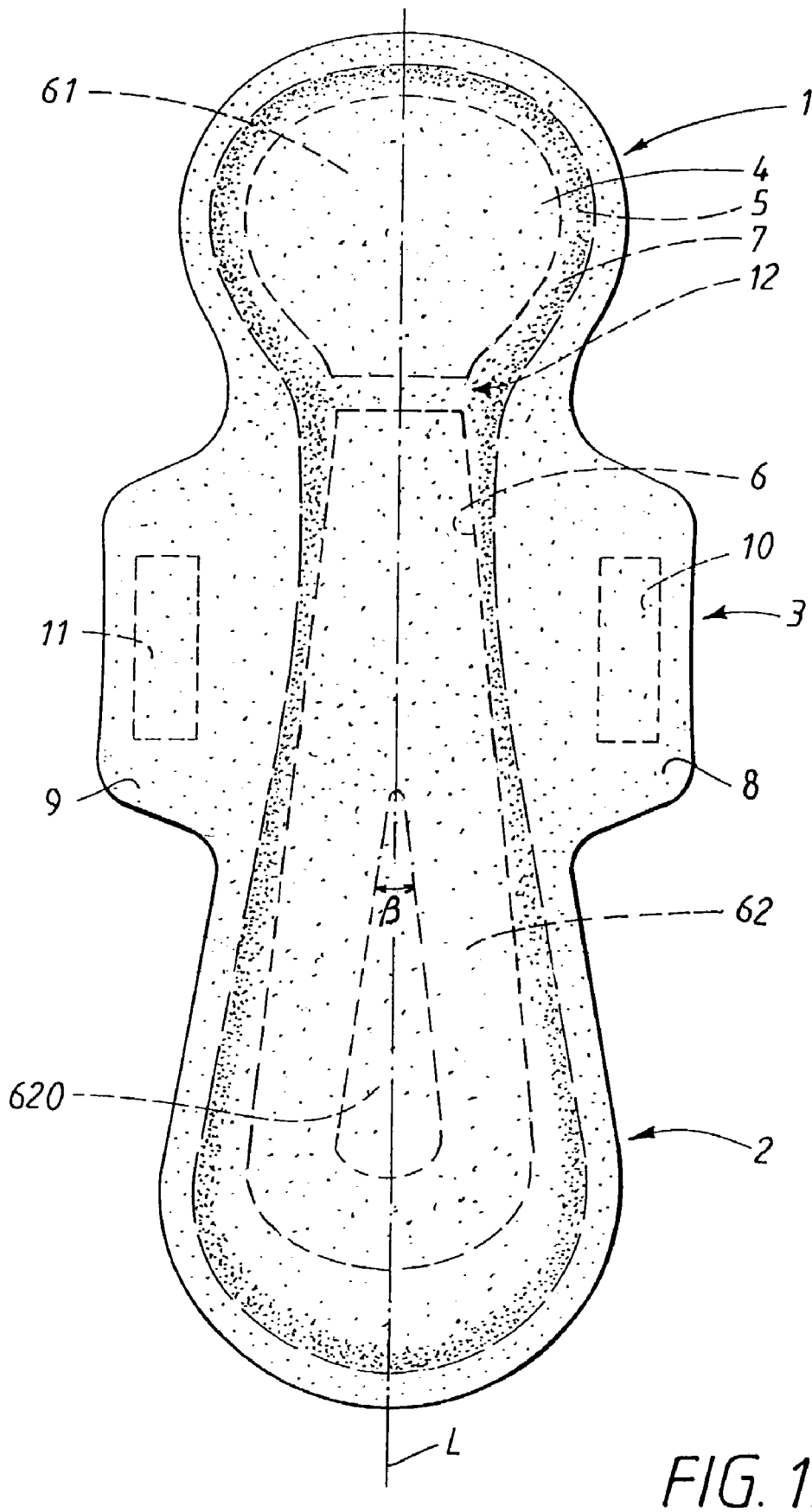
FIG. 13 shows a plan view of a further embodiment of the article according to the invention, seen towards that surface of the article which receives bodily fluids.

FIG. 13 shows an embodiment which is modified in relation to the embodiment according to FIG. 1. Those parts in the article according to FIG. 13 corresponding to similar components in the embodiment according to FIG. 1 have been provided with the same reference numbers.

The second stiffening part element 62 and therefore the absorption element also extend in over the rear portion 2 of the article. In contrast to the embodiment according to FIG. 1, the second stiffening part element 62 is continuous at the rear for increased stability. The rear portion has an elongate second through-hole 620, as a result of which a weakening is formed so that, during use, the article can fold along a longitudinal line L in the hole 620 and as a result of which the stiffening element forms legs 14 and 15 which are located on both sides of the hole 620 and are more flexible than the wider crotch portion. The legs 14 and 15 can be made slightly vertically movable in relation to one another by virtue of the width selected for the hole. The size and shape of the hole 620 are important for obtaining the desired adaptation and flexibility of the article in relation to the body. The fold formed along the hole during use of the article can penetrate the cleft between the buttocks of the wearer and in this way provides very good protection against leakage via the cleft between the buttocks, which type of leakage usually occurs during the use of conventional products when the wearer is lying on her back. The fold formed, which projects into the cleft between the buttocks of the wearer, also results in the article being stabilized in position on the wearer and remaining in the intended position during body movements, for example when the wearer is walking. The article is held in place on the wearer in both the longitudinal direction and the transverse direction by the fold formed at the hole 610. The two legs 14 and 15 are interconnected at the bottom at 145. This connection gives the second stiffening part element 62 very good stability in the rear portion and provides the article with the necessary firmness in this area.

In the illustrative embodiment shown in FIG. 13, the hole 620 is wedge-shaped and located symmetrically in relation to the longitudinal symmetry line L of the article and also forms an angle $\beta$ preferably on the order of 20°. This angle can vary within wide limits but of course depends on the design of the second part element 62. The angle $\beta$ can vary between the order of 15° and 40°.

The hole 620 is pointed at its end next to the crotch portion 3, and, in the illustrative embodiment shown, the width of the hole increases continuously from said end in the backward direction. As a result of this, the height of the fold formed will increase continuously in the same direction during use of the article, and this increasing height of the fold prevents the article being displaced forwards.

Figure 14:
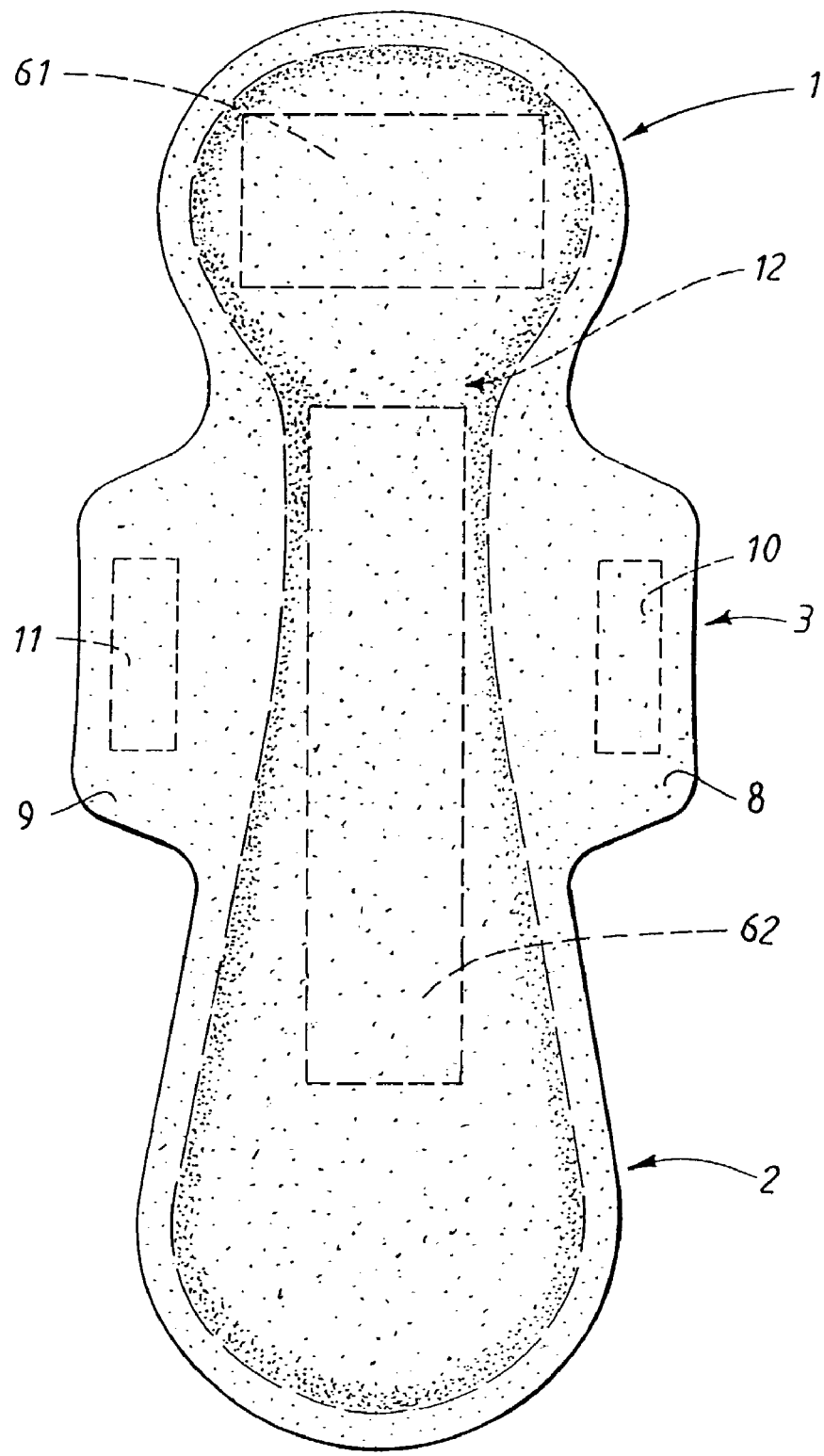
FIG. 14 shows a plan view of a further embodiment of the article according to the invention, seen towards that surface of the article which receives bodily fluids.

FIG. 14 shows a further illustrative embodiment of the article according to the invention, which illustrative embodiment differs from that shown in FIG. 1 only in that the first and second stiffening part elements are designed differently. Those parts in the article according to FIG. 14 corresponding to similar components in the embodiment according to FIG. 1 have been provided with the same reference numbers.

Here, the first, front stiffening part element 61 is of rectangular design, as can be seen from FIG. 14. In the illustrative embodiment shown here, the greatest extent of the rectangle is in the transverse direction of the article. The first part element can in fact have a different shape, such as square, oval or circular. The extent of the first part element in the transverse direction of the article is referred to as the width of the first part element. In the embodiment according to FIG. 14, it is preferable that this should be greater than the distance between the muscle tendons of the wearer on both sides of the crotch of the wearer in the groin of the latter. The second stiffening part element 62 is here of rectangular design, but other shapes are of course possible. However, from the processing point of view, a rectangular shape may be preferable if the material for forming the second part element is cut or clipped from a continuous material web. In the case of such production, a rectangular shape of the second stiffening element produces no waste.

The soft transition space 120 between the first and the second part element is here, as in other illustrative embodiments, intended to accommodate said muscle tendons on both sides of the crotch of the wearer in the groin of the latter.

The necessary distance between the first and the second stiffening part element is controlled by the width of the first part area and by its contour.

Figure 15:
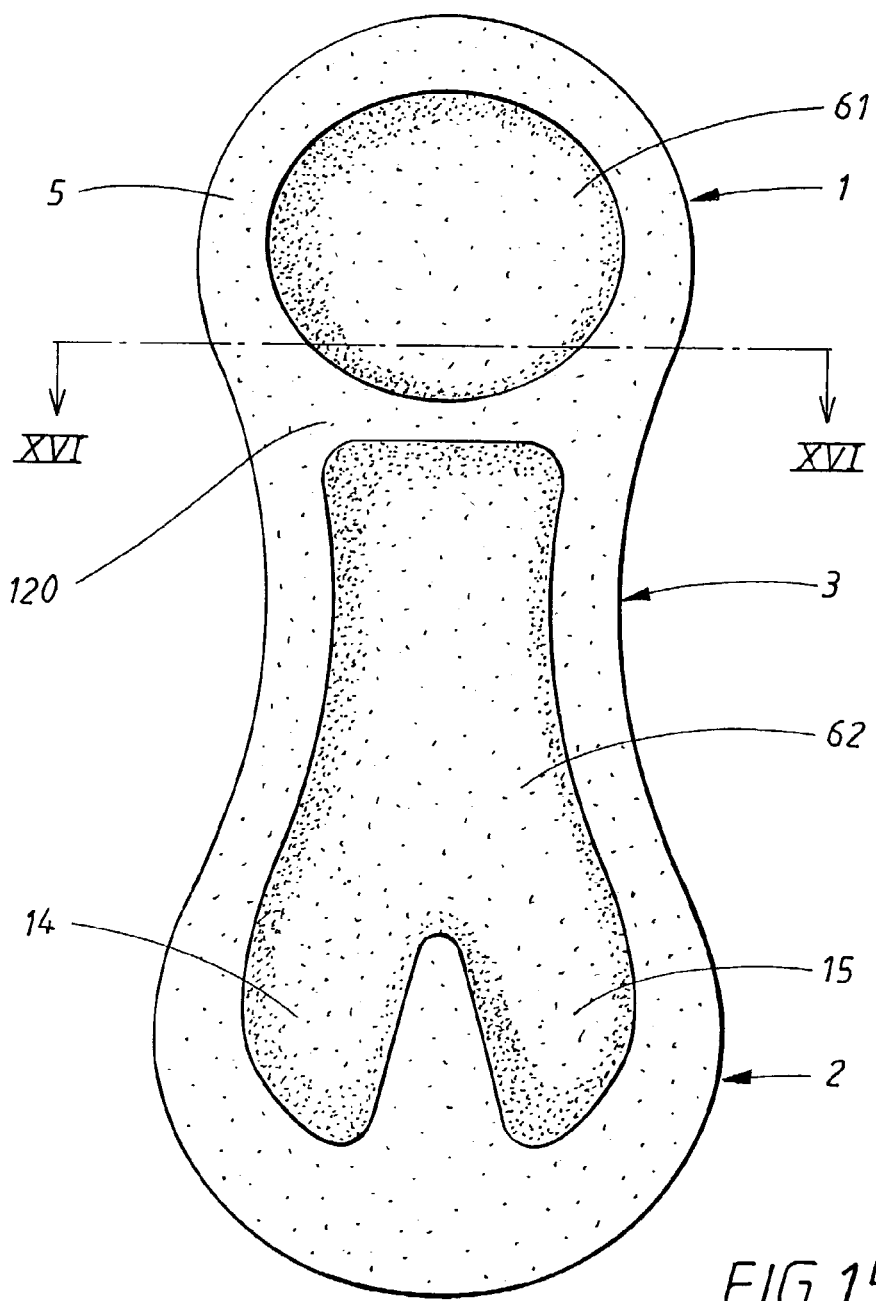
FIG. 15 shows a plan view of a further embodiment of the article according to the invention, seen towards that surface of the article which receives bodily fluids.
Figure 16:
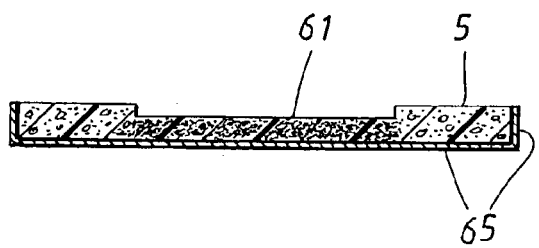
FIG. 16 shows a section along the line XVI-XVI in FIG. 15.

The embodiment shown in FIGS. 15 and 16 differs significantly from those described above. In FIGS. 15 and 16, those parts corresponding to similar components in other embodiments have been provided with the same reference numbers.

The article in the embodiment according to FIGS. 15 and 16 is made of one piece of material, for example a moulded foamed material with open pores. These pores are closed on the rear side of the article and along the entire outer edge contour to form a liquid-tight layer. This layer 65 is shown in FIG. 16. The article as a whole has an hourglass shape. The front stiffening part area 61 is circular with a diameter which exceeds the distance between said muscle tendons of the wearer.

The second stiffening part area 62 is located at a distance from the first part area 61 in such a way that a soft transition space 120 is formed, which is of such a size that said muscle tendons of the wearer are accommodated in this space.

The first and second stiffening part areas 61 and 62 in the embodiment according to FIGS. 15 and 16 have been brought about by permanent compression of the foamed material in these areas. The second stiffening part area extends over the crotch portion 3 of the article and in over the rear portion 2, where the second stiffening part area becomes two leg portions 14, 15.

To increase the absorption capacity, the second stiffening part area (and, if appropriate, the first stiffening part area) can include particles of a highly absorbent material which is added in conjunction with the forming of the product.

In the illustrative embodiment shown in connection with FIGS. 15 and 16, the article has been assumed to constitute a complete article. It is of course possible to omit the formation of a liquid-tight layer made of the foamed material and to complete an hourglass-shaped foam body, partly compressed to form the part areas, with a covering of such a type as was described in connection with, for example, the embodiment shown in FIG. 1, that is to say with a liquid-permeable inner layer made of non-woven and a liquid-tight outer layer made of a plastic film such as polyethylene.

The invention is not limited to the illustrative embodiments described above, but a large number of modifications are possible within the scope of the patent claims below.

For example, anatomically shaped stiffening and absorbent part elements of the type described above can be arranged in what are known as pant nappies, that is to say where the nappy is integrated into disposable pants.

It has been stated above that the stiffening absorbent part elements can be made from different materials and from laminates made of one or more material(s). The stiffening absorbent part elements can also be made from more than one layer and with the extent of the individual layers being different, in which way it is possible for different areas of the stiffening element to have different stiffness.

As mentioned above, the stiffening element can consist of all the material layers and bonding agents included. Different stiffness in different areas of the stiffening element can therefore also be obtained by varying the degree of connection in different areas, for example different quantities of adhesive in different areas and even the absence of adhesive or other bonding agent in different areas between or in individual layers.

The elastic means 16, which is arranged in the cutout 13, has been indicated in the illustrative embodiments described above as having been arranged in a pretensioned state. However, in the manufacture of absorbent articles such as sanitary towels, nappies and the like, it is known to arrange a heat-sensitive elastic means in an untensioned state and to tension the elastic by heat treatment. This suitably takes place when the articles are packed.

In the illustrative embodiments described above relating to articles for arrangement inside the crotch portion of briefs, the article is in the majority of the illustrative embodiments provided with permanently arranged wings for attachment of the article to the briefs with the wings folded around the edge portion of the briefs and attached on the outside of the crotch portion. The wings can consist of separate elements which are attached to the rest of the article in connection with the article being put on. The separate wings can be arranged detachably on the rest of the article during manufacture of the article, as a result of which a wearer who does not want to have wings on the article can remove these in connection with putting the article on.

The illustrative embodiments described above which do not have wings can be provided with separate wings either during manufacture or when the article is put on.

The invention claimed is:

1. Absorbent article having a longitudinal direction and a transverse direction, a front portion, a rear portion, a crotch portion located between the rear portion and the front portion, an absorbent element and a liquid-tight layer, and at least two stiffening elements which are intended to contribute to the three-dimensional shape of the article during its use, wherein the stiffening elements each form a single plane before use of the article,
   wherein the stiffening elements comprise, in the longitudinal direction of the article, a first, front stiffening part area in the front portion of the article and at least one further, second stiffening part area which is a separate and distinct element from the first stiffening part area, said second stiffening part area being discontinuous from said first stiffening part area,
   wherein said first stiffening part area is spaced from said second stiffening part area at least at a transition between the crotch portion and the front portion such that a transition gap is formed between a rearward edge of the first stiffening part area and a forward edge of the second stiffening part area, said gap being defined by the absence of said stiffening element therein, and defining a bending indication and a distance between said first and second stiffening parts of approximately 10 mm-45 mm, said separate first and second stiffening part areas and transition gap being arranged so as to control the positioning of the article on the wearer, the width of the first stiffening part area exceeding 25 mm, and the transition gap between the first and second stiffening part areas being arranged to as to come to lie directly in front of said muscle tendons of the wearer.

2. Article according to claim 1, wherein the first and the second stiffening part areas are separated from one another at said transition by a distance on the order of 15-45 mm.

3. Article according to claim 1, wherein the width of the second stiffening part area close to said gap or at least at some point along the crotch portion of the article exceeds the distance between muscle tendons of a wearer on both sides of the crotch of the wearer in the groin of the latter.

4. Article according to claim 1, wherein the distance between the stiffening part areas is controlled by the width of the front part area and by its contour.

5. Article according to claim 4, wherein the side edges of the first stiffening part area diverge in the direction from said transition, and the side edges of the first stiffening part area form, in the direction from the crotch portion, an acute angle (α) with a line in the longitudinal direction of the article.

6. Article according to claim 5, wherein the second stiffening part area extends part of the way in over the rear portion of the article, and the side edges of the second stiffening part area diverge in the direction from the crotch portion at least part of the way from the crotch portion in over the rear portion of the article.

7. Article according to claim 6, wherein the second stiffening part area has in the rear portion a cutout extending from its end edge in the direction towards the crotch portion, as a result of which the article is during use provided with a fold along the longitudinal direction of the article in said cutout, which fold extends into the cleft between the buttocks of the wearer during use of the article.

8. Article according to claim 7, wherein said cutout is wedge-shaped and located symmetrically and forms an angle (β) of between 10 and 120° at its end facing the crotch portion.

9. Article according to claim 8, wherein the angle (β) is between 15 and 40°.

10. Article according to claim 1, wherein said stiffening part areas include compressed part areas of a continuous material body made in one piece, which forms said soft transition space between said stiffening part areas.

11. Article according to claim 1, wherein the first stiffening part area and the second stiffening part area are made from materials that are different from each other.

12. Article according to claim 1, wherein the first and the second stiffening part areas have stiffnesses that are different from each other.

13. Article according to claim 1, wherein the first and the second stiffening part areas have absorptions and swelling capacities that are different from each other.

14. Article according to claim 1, wherein the first part area is non-absorbent so as to maintain its three-dimensional shape during use.

15. Article according to claim 1, wherein the first stiffening part area is absorbent and the second stiffening part area is non-absorbent.

16. Article according to claim 1, wherein the first and the second stiffening elements are connected by an elastic element.

17. Article according to claim 1, wherein at least the second of said stiffening part areas comprises a second stiffening element that is absorbent and at the same time constitutes the absorbent element, and it swells during absorption while on the whole retaining its geometry in the transverse direction of the article.

18. Article according to claim 1, wherein at least one of the stiffening part areas has a stiffness in the dry state on the order of 1-15 N measured according to ASTM D 4032-82.

19. Article according to claim 1, wherein the side edges of the first stiffening part area diverge at least part of the way from the crotch portion in over the front portion of the article and are arranged so as to form an angle (α) between a line in the longitudinal direction of the article and each of said side edges on the order of 35-55°.

20. Article according to claim 19, wherein the angle (α) is on the order of 45°.

21. Article according to claim 1, wherein at least the second stiffening part area also constitutes the absorbent element, and at least the first stiffening part area has a stiffness of at least 1.0 N and is designed with essentially the same stiffness over the entire extent of the stiffening part area.

22. Article according to claim 1, further comprising a hump-forming element made of a resilient material arranged under said second stiffening part area over at least part of the crotch portion, which hump-forming element is arranged so as to bring about a raised portion on the side which is intended to be fitted against the wearer, the raised portion being arranged so as to come to lie directly in front of the genitals of the wearer after fitting of the article on the wearer.

23. Article according to claim 22, wherein the raised portion is elongate in the longitudinal direction of the article and has a length of between 20 mm and 120 mm.

24. Article according to claim 22, wherein the raised portion is narrower than a remainder of the article in the crotch area, and the raised portion is at least twice as thick as surrounding areas.

25. Article according to claim 1, further comprising an elastic means arranged in the longitudinal direction of the article and centrally along the rear portion of the article and along at least part thereof from the crotch portion, which elastic means is intended, along its length, to draw adjacent material portions together and curve the article upwards for better contact with the body of the wearer.

26. Article according to claim 1, wherein the first stiffening part area comprises a first stiffening element that serves as an absorption means, or the second stiffening part area comprises a second stiffening element that serves as an absorption means, or both, and wherein the absorption means has very great liquid-spreading capacity for spreading bodily fluid received in the relatively narrow crotch area bounded by the anatomy of the wearer directly in front of the genitals of the wearer over the absorbent portions of the whole article, and the first stiffening part element, or the second stiffening part element, or both is designed with great swelling capacity in the depth direction and attendant great absorption capacity.

27. Article according to claim 26, wherein at least one of said stiffening part areas comprises a stiffening part element that also serves as an absorption element and is essentially homogeneous over its entire extent with regard to thickness, stiffness, spreading capacity and absorption capacity, as a result of which said stiffening part area and thus also the absorption element curve evenly during use without forming local irregularities which may give rise to undesirable spreading of liquid.

28. Article according to claim 27, wherein the second stiffening part area also constitutes the absorbent element, and the width of the second stiffening part area after said transition increases continuously in the crotch portion in the backward direction towards the rear portion for the purpose of optimally utilizing available width space in this area with regard to maximum absorption.

29. Article according to claim 1, wherein the article is arranged so as, by virtue of the stiffness selected for said stiffening part areas and by virtue of the selection of said geometry and dimensions in and around the transition between the crotch portion and the front portion, when the article is positioned in connection with it being put on with the transition between the front portion and the crotch portion between said muscle tendons, to be fixed in between these and in this way be transformed from plane form to three-dimensional form with the front portion curved upwards in relation to the crotch portion and forming a bowl-like shape at least in an area next to the crotch portion.

30. Absorbent article according to claim 1, wherein within their areas of delimitation, said stiffening part areas have regions of low or no stiffness.

31. Article according to claim 1, wherein said stiffening part areas include part areas of a body made in one piece from foamed material, which part areas are compressed and bonded in compressed state.

32. Article according to claim 1, wherein at least one of said stiffening part areas includes a separate stiffening part element.

33. Article according to claim 32, wherein said separate stiffening part element also serves as an absorbent element and has a number of interconnected tissue layers with, arranged between the layers, superabsorbent material in the form of particles or fibres.

34. Article according to claim 32, wherein a first stiffening part element has a first through-hole which is oblong and extends in the longitudinal direction of the article and along the centre line of the article, and which makes possible resilient compression in the lateral direction of the first stiffening part element when lateral forces act against the side edges of the first part element.

35. Article according to claim 34, wherein a second stiffening part element has, in the crotch portion, an elongate second through-hole along the longitudinal centre line of the article, which second hole makes possible resilient compression in the lateral direction of the second stiffening part element in the crotch area of the article when lateral forces act against the crotch portion during use of the article.

36. Article according to claim 35, wherein the second stiffening part element has an elongate portion in the rear portion of the article, and an elongate third through-hole extends in the longitudinal direction of the article in said portion, as a result of which the article is during use provided with a fold along the longitudinal direction of the article along said hole, which fold extends into the cleft between the buttocks of the wearer during use of the article.

37. Article according to claim 1, wherein said absorbent article is selected from the group consisting of a sanitary towel, a panty liner, an incontinence pad, and a nappy.

38. Article according to claim 1, wherein said transition gap is defined by a lack of said stiffening elements at said gap.

* * * * *

UNITED STATES PATENT AND TRADEMARK OFFICE
CERTIFICATE OF CORRECTION

PATENT NO.       : 7,601,144 B2                        Page 1 of 1
APPLICATION NO.  : 10/310907
DATED            : October 13, 2009
INVENTOR(S)      : Solgun Drevik It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 926 days.

Signed and Sealed this

Fifth Day of October, 2010

David J. Kappos
*Director of the United States Patent and Trademark Office*